(12) United States Patent
Willard et al.

(10) Patent No.: US 12,285,189 B2
(45) Date of Patent: Apr. 29, 2025

(54) HIP ACCESS PORTAL SAVER

(71) Applicant: Conmed Corporation, Utica, NY (US)

(72) Inventors: Benjamin Willard, Clearwater, FL (US); Eric Stubkjaer, Gulfport, FL (US); Thomas Kehoe, Tarpon Springs, FL (US); Kevin Quintero, Safety Harbor, FL (US)

(73) Assignee: Conmed Corporation, Utica, NY (US)

( * ) Notice: Subject to any disclaimer, the term of this patent is extended or adjusted under 35 U.S.C. 154(b) by 350 days.

(21) Appl. No.: 16/771,811

(22) PCT Filed: Dec. 13, 2018

(86) PCT No.: PCT/US2018/065419
§ 371 (c)(1),
(2) Date: Jun. 11, 2020

(87) PCT Pub. No.: WO2019/118703
PCT Pub. Date: Jun. 20, 2019

(65) Prior Publication Data
US 2021/0169522 A1    Jun. 10, 2021

Related U.S. Application Data

(60) Provisional application No. 62/673,520, filed on May 18, 2018, provisional application No. 62/673,365, (Continued)

(51) Int. Cl.
*A61B 17/34* (2006.01)
*A61B 17/00* (2006.01)

(52) U.S. Cl.
CPC ...... *A61B 17/3462* (2013.01); *A61B 2017/00955* (2013.01); *A61B 2017/00991* (2013.01); *A61B 2017/3464* (2013.01); *A61B 2017/349* (2013.01)

(58) Field of Classification Search
CPC ............ A61B 17/3462; A61B 17/3417; A61B 17/3439; A61B 2017/00955;
(Continued)

(56) References Cited

U.S. PATENT DOCUMENTS 4,716,901 A * 1/1988 Jackson ............. A61B 17/3439
606/198
5,957,888 A * 9/1999 Hinchliffe .......... A61B 17/3421
606/174
(Continued)

FOREIGN PATENT DOCUMENTS

EP      2381869       11/2011
JP    2008-049162 A2   3/2008
(Continued)

OTHER PUBLICATIONS

International Search Report Form PCT/ISA/220, International Application No. PCT/US2018/065419, pp. 1-17, dated Feb. 5, 2019.
(Continued)

*Primary Examiner* — Brigid K Byrd
(74) *Attorney, Agent, or Firm* — Bond, Schoeneck & King, PLLC; Frederick J. M. Price

(57) ABSTRACT

A portal saver device for installing a flexible cannulated tube at a surgical site. A portal saver device includes an obturator. The obturator has an obturator body having a cannulated outer obturator tube extending therethrough. The outer obturator tube has a distal tip with a dilating assembly movable between a collapsed, first configuration and an expanded, second configuration. A shaft expander has a cannulated inner obturator tube, which is movable between a first position and a second position within the outer obturator tube. In the first position, the inner obturator tube is retracted from the distal tip of the outer obturator tube and the dilating assembly is in the first configuration. In the second position, the inner obturator tube is advanced within the distal tip of
(Continued)

the outer obturator tube and the dilating assembly is in the second configuration.

9 Claims, 34 Drawing Sheets

Related U.S. Application Data filed on May 18, 2018, provisional application No. 62/673,541, filed on May 18, 2018, provisional application No. 62/673,451, filed on May 18, 2018, provisional application No. 62/598,094, filed on Dec. 13, 2017.

(58) Field of Classification Search
CPC .... A61B 2017/00991; A61B 2017/349; A61B 2017/3443; A61B 2017/3454; A61B 2017/346
See application file for complete search history.

(56) References Cited

U.S. PATENT DOCUMENTS

| | | | | |
|---|---|---|---|---|
| 5,971,960 | A * | 10/1999 | Flom | A61B 17/3417 604/174 |
| 6,022,367 | A * | 2/2000 | Sherts | A61B 17/32053 606/184 |
| 6,030,364 | A * | 2/2000 | Durgin | A61B 17/3417 604/27 |
| 8,425,532 | B2 | 4/2013 | Flom et al. | |
| 8,517,932 | B2 | 8/2013 | Sakai, Jr. et al. | |
| 8,795,235 | B2 | 8/2014 | Mastri et al. | |
| 2004/0082969 | A1* | 4/2004 | Kerr | A61B 17/0218 606/205 |
| 2004/0199121 | A1* | 10/2004 | Wenchell | A61B 17/3439 604/167.06 |
| 2005/0119685 | A1 | 6/2005 | Smith | |
| 2006/0100501 | A1* | 5/2006 | Berkelman | A61B 90/50 600/415 |
| 2007/0088277 | A1* | 4/2007 | McGinley | A61B 17/0218 604/167.01 |
| 2008/0086167 | A1* | 4/2008 | Mastri | A61B 17/3421 606/198 |
| 2008/0262383 | A1 | 10/2008 | Routhier et al. | |
| 2009/0306586 | A1* | 12/2009 | Ross | A61B 17/3439 604/93.01 |
| 2011/0144447 | A1* | 6/2011 | Schleitweiler | A61B 17/3421 600/210 |
| 2011/0144448 | A1* | 6/2011 | Shelton, IV | A61B 17/3423 600/216 |
| 2011/0174425 | A1 | 7/2011 | Moreno et al. | |
| 2011/0224619 | A1* | 9/2011 | Weststrate | A61J 15/0038 604/175 |
| 2013/0267989 | A1* | 10/2013 | Mauldin | A61M 29/00 606/86 R |
| 2015/0065808 | A1 | 3/2015 | Van Wyk et al. | |

FOREIGN PATENT DOCUMENTS

| | | |
|---|---|---|
| JP | 2012-510878 A2 | 5/2012 |
| JP | 2012532661 A | 12/2012 |
| JP | 2013244411 A | 12/2013 |
| JP | 2011539754 A | 9/2014 |
| KR | 20210057754 A | 5/2021 |
| WO | WO 2006/017507 | 2/2006 |

OTHER PUBLICATIONS

JP Office Action, dated Jun. 29, 2021, Application No. 2020-531737, pp. 1-14.
JP Office Action, dated Dec. 21, 2022, Application No. 2021-185532, pp. 1-8.
AU Exam Report, dated Oct. 21, 2022, Application No. 2021215217, pp. 1-6.
Korean Office Action, Application No. 10-2020-7017033, dated Mar. 24, 2023, pp. 1-5.
Translated KR Office Patent Decision, App. No. 10-2020-7017033, dated Mar. 7, 2024, pp. 1-6.

* cited by examiner

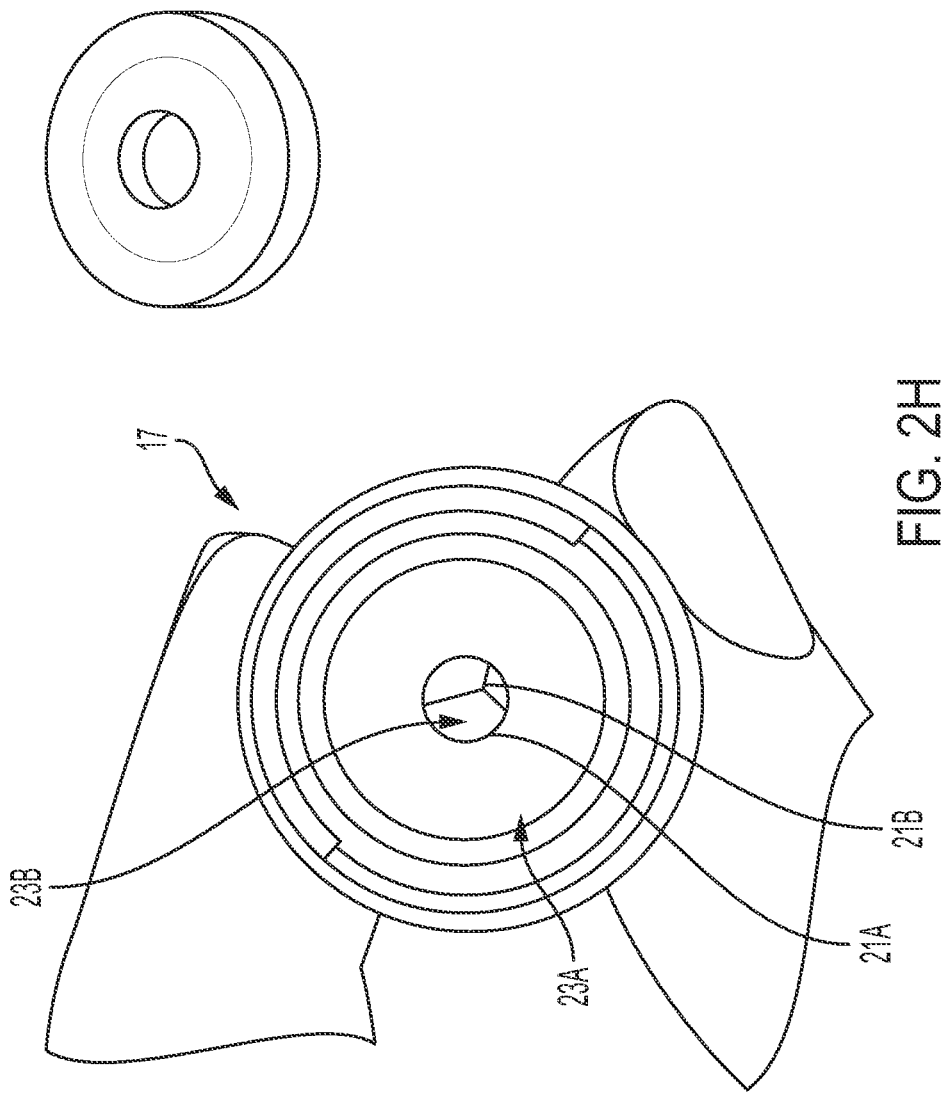

HIP ACCESS PORTAL SAVER

CROSS-REFERENCES TO RELATED APPLICATIONS

This application is a national stage application under 35 U.S.C. 371 based on international patent application PCT/US18/65419 filed on Dec. 13, 2018, which relates and claims priority to U.S. Provisional Application No. 62/598,094, filed Dec. 13, 2017, and entitled "Baggula Hip Access Portal Saver," U.S. Provisional Application No. 62/673,365, filed May 18, 2018, and entitled "Expanding Mechanism for Cannula Dermal Fixation," U.S. Provisional Application No. 62/673,451, filed May 18, 2018, and entitled "Adhesive Disc for Cannula Dermal Fixation, U.S. Provisional Application No. 62/673,541, filed May 18, 2018, and entitled "Adhesive Disc for Cannula Dermal Fixation," and U.S. Provisional Application No. 62/673,520, filed May 18, 2018, and entitled "Suction Cup for Cannula Dermal Fixation."

BACKGROUND OF THE INVENTION

1. Field of the Invention

The present disclosure is directed generally to a portal saver device and, more particularly, to an obturator with a dilating assembly for accommodating instruments of various sizes and geometries.

2. Description of Related Art

In order to maintain arthroscopic intra-articular hip joint access, a series of access tools (switching stick, slotted cannula, disposable cannula, etc.) are conventionally used frequently for insertion and removal of the instruments performing work on the patient. The use of access tools account for a great percentage of the time spent in procedure by the surgeon. During the time spent using the access tools, the surgeon is not performing any actual work on the patient's pathology.

A common access tool in the field of arthroscopic surgery is a "cannula." The cannula is used to maintain an open portal leading from outside the patient's body to inside the body to the location where the arthroscopic procedure is to be performed. It is important that this cannula stay inside the body, maintain this path, and not fall out, migrate outward, or migrate farther inward. This is accomplished by a number of means today, most frequently by placing aggressive threads on the outside of the cannula to auger (or drill) into the dermal layer and tissue below it. This can require a sizable incision be made to admit such screw threads, resulting in a corresponding-sized scar.

Current cannulas 1, such as those shown in FIGS. 1A-1C, mostly use mechanical threads 2 on the exterior 3 of the tube-like body 4 of the cannula 1 itself. FIG. 1A shows a standard cannula 1 with a stiff tube-like body 4. The cannula 1 in FIG. 1B is less rigid than that shown in FIG. 1A, but the tube-like body 4 has virtually no radial movement. FIG. 1C shows a cannula 1 which is more flexible than that shown in FIG. 1B; however, the cannula 1 in FIG. 1C is semi-flexible but cannot accommodate a wide range of instruments. Conventional cannulas 1 have a fluid seal 5 on the proximal end to prevent the leakage of fluid from the surgical site. Some cannulas have indicators 6, as also shown in FIG. 1C, along the tube-like body 4 for customizing the size of the tube-like body 4. These cannulas are often screwed in with an obturator.

Current surgical procedures require instrumentation to be inserted and removed from the patient multiple times (through numerous portals). For example, in a hip surgical procedure, a surgeon must work through 2-3 portals and the portals in the hip are typically 4-6 inches long. Through these hip portals, the surgeon cannot simply remove an instrument/scope and move to another portal. It requires 2-3 different instruments (and approximately 9 steps or actions) to move the main instrument/scope between portals and this is done many times throughout an entire surgical (e.g., hip) procedure. The current cannulas on the market, such as those shown in FIGS. 1A-1C, are too rigid and restrict movement and as a result, surgeons do not use these throughout the whole procedure. Cannulas are typically only used at the end of the procedure for placing anchors and passing suture.

Therefore, a need exists for a flexible portal saver device that allows for easy insertion and removal of instruments from a surgical site.

Some cannulas alternatively or additionally have barbs, and these cannulas can be inserted straight into the surgical site while benefiting from a bit of oscillating rotation during advancement into the body. Still, cannulas use a collapsing accordion-like member which can be stretched to decrease its diameter and compressed to increase its diameter. None of these conventional cannulas, however, provide the large displacement of rigid bodies sub-dermally that allow insertion and subsequent removal through a small incision. Further, none of these conventional cannulas provide for a small incision size or minimize trauma to the region surrounding the incision site. Even further, none of the conventional cannulas provide a wide a range of motion and freedom.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

Embodiments of the present invention recognize that there are potential problems and/or disadvantages with the conventional cannulas and access tools. For example, the exterior aggressive threads on conventional cannulas can cause additional trauma to an incision site (as described above). Therefore, a need exists for a portal saver device that allows for removal through a small incision and that minimizes trauma at the incision site. Various embodiments of the present invention may be advantageous in that they may solve or reduce one or more of the potential problems and/or disadvantages discussed herein.

The present disclosure is directed to an inventive configuration, structure, and resulting function of a portal saver assembly and a method for installing a flexible cannulated tube at a surgical site. According to one aspect, the portal saver assembly includes an obturator. The obturator can have an obturator body with a cannulated outer obturator tube extending therethrough. The outer obturator tube can have a distal tip with a dilating assembly movable between a collapsed, first configuration and an expanded, second configuration. A shaft expander can have a cannulated inner obturator tube, which is movable between a first position and a second position within the outer obturator tube. In the first position, the inner obturator tube is retracted from the distal tip of the outer obturator tube and the dilating assembly is in the first configuration. In the second position, the inner obturator tube is advanced within the distal tip of the outer obturator tube and the dilating assembly is in the second configuration.

According to an embodiment, the dilating assembly is a duck bill portion at the distal tip of the outer obturator tube. The duck bill portion has at least two arms composed of the outer obturator tube.

According to an embodiment, the obturator also includes an actuator such as a post on the inner obturator tube which forces the at least two arms radially outward from the collapsed, first configuration to the expanded, second configuration.

According to an embodiment, the outer obturator tube extends past a distal end of the obturator body.

According to an embodiment, the obturator includes a cannulated tube which extends around the outer obturator tube distal the obturator body.

According to an embodiment, the obturator includes a pair of stirrups extending proximally from the cannulated tube.

According to an embodiment, the pair of stirrups is removably attached to the obturator body via one or more connectors.

According to an embodiment, the obturator includes a stirrup release actuator on the obturator body configured to release the pair of stirrups from the one or more connectors.

According to an embodiment, the cannulated tube is composed of a flat sheet material with a pair of seams extending along a length of the cannulated tube.

According to an embodiment, the cannulated tube has a flattened section between two rounded sections.

According to an embodiment, the obturator includes a rigid body connected around the cannulated tube, which is moveable along a length of the cannulated tube.

According to an embodiment, the rigid body comprises a proximal telescoping assembly and distal exterior barbs.

According to an embodiment, the proximal telescoping assembly comprises one or more blades.

According to an another aspect, a method for installing a cannulated tube includes (but is not limited to) the steps of: (i) providing an obturator comprising an obturator body having a cannulated outer obturator tube extending therethrough and past a distal end of the obturator body, a shaft expander comprising a cannulated inner obturator tube which is movable within the outer obturator tube, a cannulated tube around the outer obturator tube distal the obturator body, and a rigid body; (ii) advancing the cannulated tube within a surgical incision; (iii) sliding the rigid body along the cannulated tube; (iv) fixing the rigid body under a dermal layer; (v) adjusting a length of the cannulated tube; and (vi) removing the obturator from the cannulated tube.

According to an embodiment, the rigid body comprises a proximal telescoping assembly with a blade and distal exterior barbs. The exterior barbs are configured to grip the dermal layer.

According to an embodiment, the step of adjusting the length of the cannulated tube includes the step of moving the telescoping assembly along the cannulated tube and cutting the cannulating tube with the blade.

According to an embodiment, a pair of stirrups extend proximally from the cannulated tube.

According to an embodiment, the method includes the step of removably attaching the pair of stirrups to the obturator body via one or more connectors.

According to an embodiment, the obturator includes a stirrup release actuator on the obturator body.

According to an embodiment, the step of removing the obturator from the cannulated tube includes the step of actuating the stirrup release actuator on the obturator body.

According to one aspect, the portal saver assembly includes a portal saver device. The portal saver device includes a tubular flexible body extending distally from a dermal threaded body, wherein the tubular flexible body is movable radially with respect to the dermal threaded body, and a first seal and a second seal connected to the dermal threaded body.

According to an embodiment, the tubular flexible body is composed of thermoplastic urethane (TPU).

According to an embodiment, the portal saver device includes external threads on the dermal threaded body.

According to an embodiment, the first seal comprises a circular opening.

According to an embodiment, the second seal comprises an opening formed from three slits converging at a central location.

According to an embodiment, the tubular flexible body comprises a seal along its length.

According to an embodiment, the tubular flexible body is a single continuous piece of material.

BRIEF DESCRIPTION OF THE DRAWINGS

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments.

Reference is now made briefly to the accompanying drawings, in which:

FIG. 2H is a front view schematic representation of a double seal, according to an embodiment;

DETAILED DESCRIPTION OF THE INVENTION

Figure 1A:
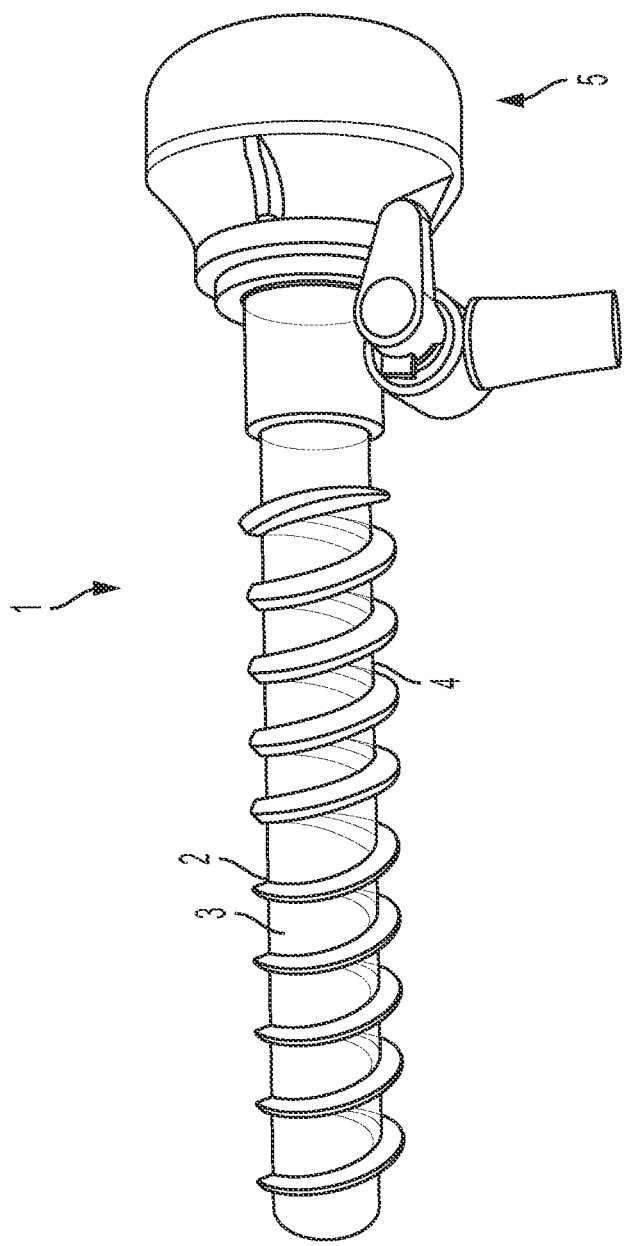
FIG. 1A is a perspective view schematic representation of a cannula of the prior art.
Figure 1B:
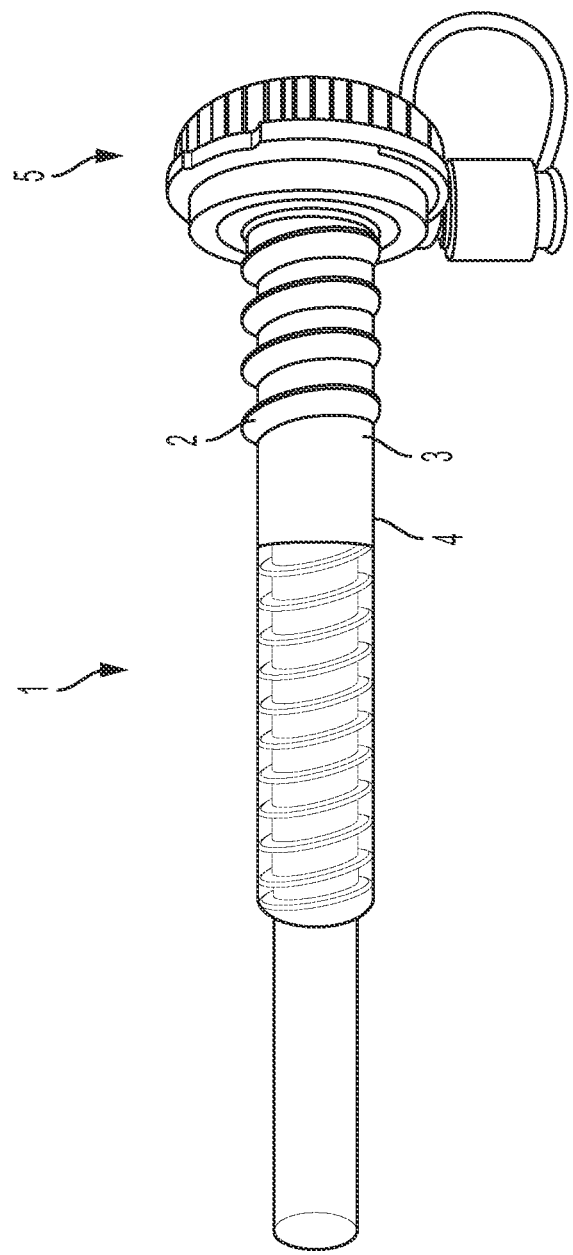
FIG. 1B is a perspective view schematic representation of another cannula of the prior art.
Figure 1C:
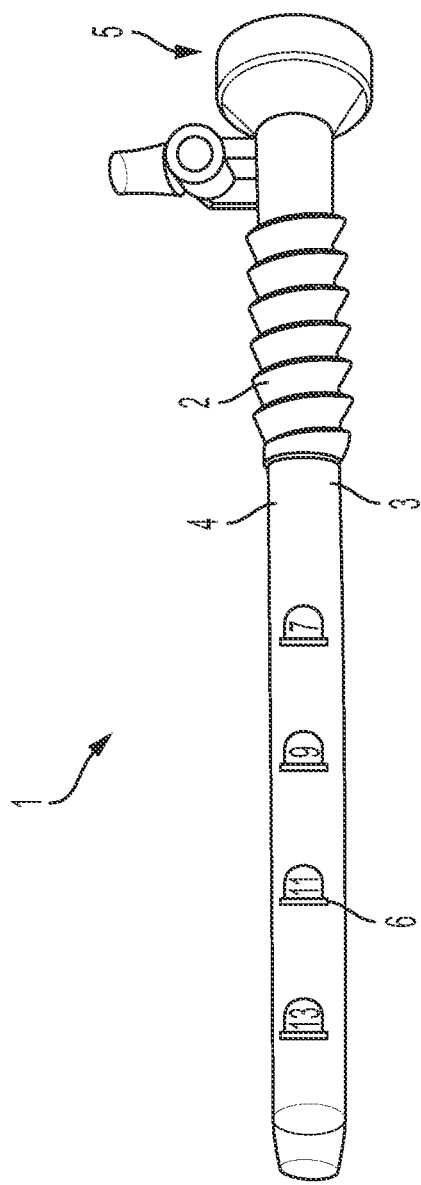
FIG. 1C is a perspective view schematic representation of yet another cannula of the prior art.

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Referring now to the figures, wherein like reference numerals refer to like parts throughout, FIGS. 2A-2J are various views schematic representations of a portal saver device 16, according to an embodiment. The portal saver device 14 in FIGS. 2A-2B comprises a tube-like (or cannulated) flexible body 11 extending distally from a dermal threaded body 13 (with a fluid seal 17). In the embodiment depicted in FIG. 2A, the portal saver device 14 comprises indicators 15 along the flexible body 11 for customizing the size of the flexible body 11. The portal saver device 14 maintains the path from outside the body (e.g., the skin) to the surgical site (e.g., the joint), which allows the surgeon to move an instrument from one portal to another in two steps or actions (as opposed to 9 steps or actions with conventional devices). In the embodiment depicted in FIG. 2B, the flexible body 11 is formed via extrusion. However, in alternative embodiments, there are one or more seals along a length of the flexible body 11. The seals can be angled or perpendicular to each other along the longitudinal axis of the flexible body 11 (which is approximately parallel to the length to the flexible body 11).

Figure 2A:
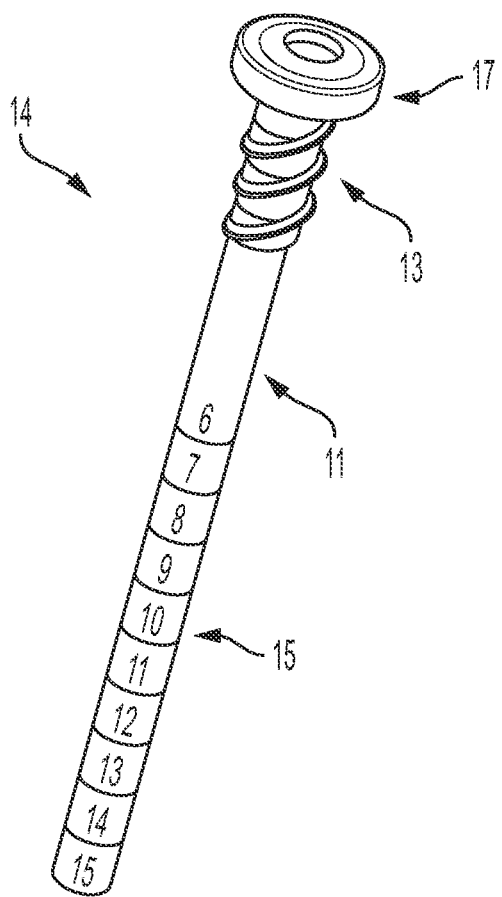
FIG. 2A is a perspective view schematic representation of a portal saver device, according to an embodiment.
Figure 2B:
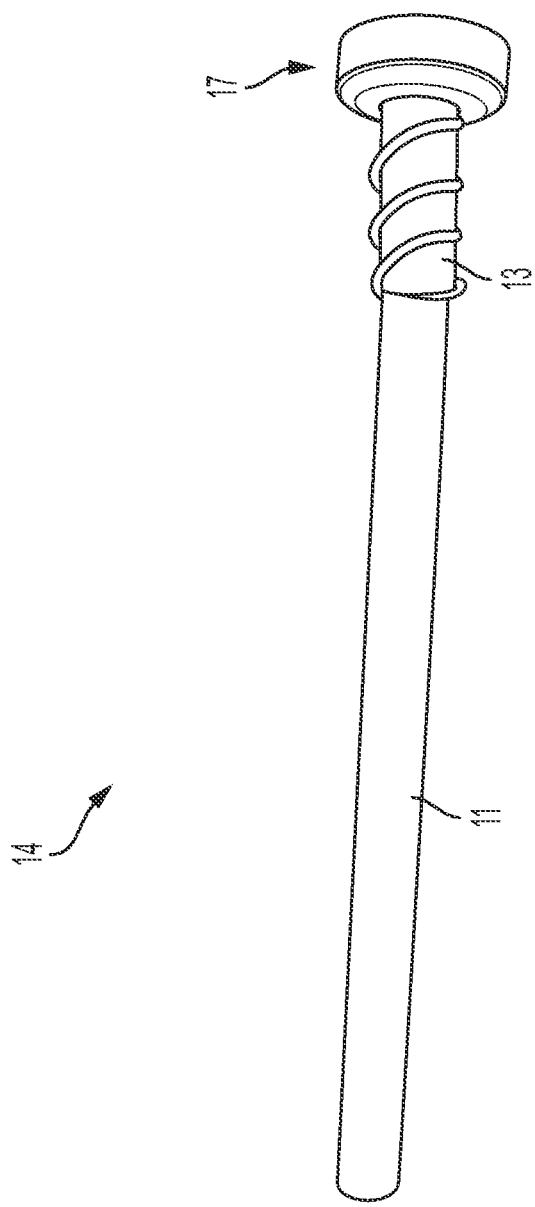
FIG. 2B is another perspective view schematic representation of a portal saver device, according to an embodiment.

The flexible body 11 of FIGS. 2A-2B can be composed of thermoplastic urethane (hereinafter "TPU")). TPU is a thermoplastic elastomer comprising block copolymers. Specifically, TPU comprises linear alternating hard segments and soft segments—as should be understood by those of ordinary skill in the art. The hard segments are composed of diisocyanates with short-chain diols (i.e., "chain extenders"), making them short, high polarity segments. The soft segments are composed of diisocyanates with long-chain diols, making them long, low polarity segments. The rigidity of TPU can be fine-tuned by increasing or decreasing the ratio of hard segments to soft segments. TPU has high mechanical properties, high heat resistance, high resistance to mineral oils, high hydrolysis resistance, high low-temperature flexibility, high resistance to microbiological degradation, and high elasticity across the entire hardness range. TPU has a hardness of 30 Shore A to 60 Shore D under standard atmospheric conditions—as should be understood by those of ordinary skill in the art in conjunction with a review of this disclosure. An example of TPU is Elastollan®. Another example of TPU is Isothane grade 5090A, made by Greco.

Figure 2C:
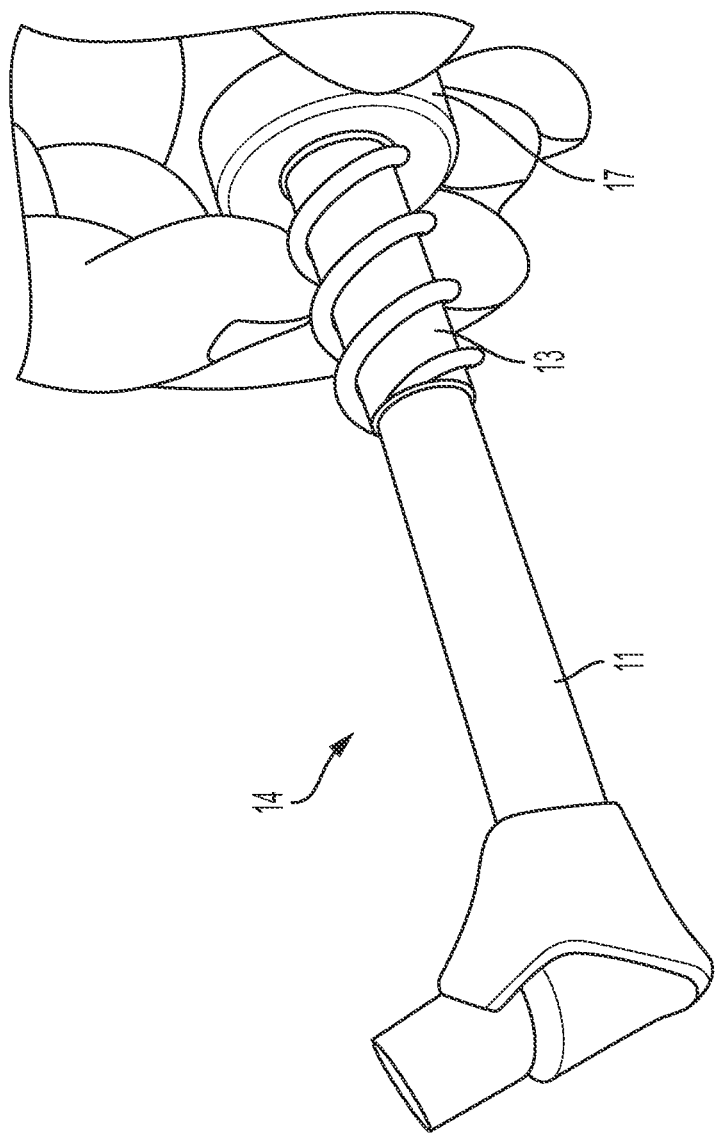
FIG. 2C is a perspective view schematic representation of the portal saver device of FIG. 2B with the flexible body in a knotted configuration.
Figure 2D:
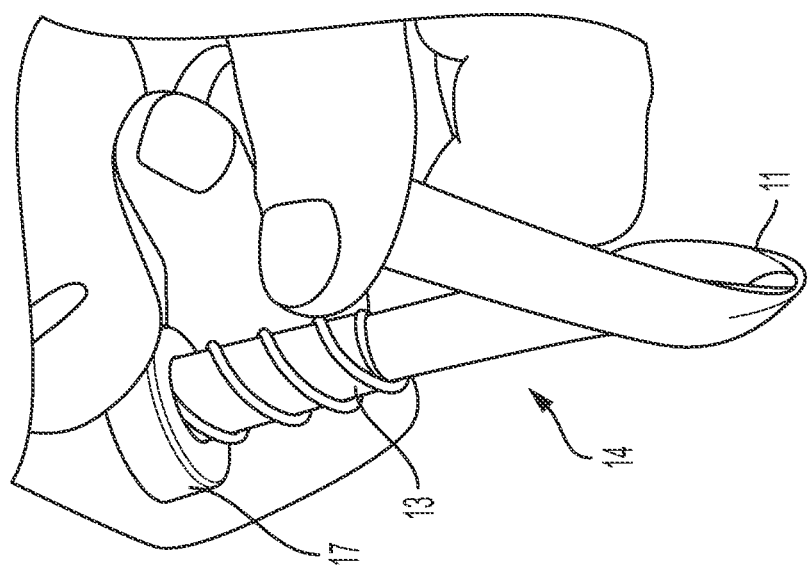
FIG. 2D is a perspective view schematic representation of the portal saver device of FIG. 2B with the flexible body in a twisted configuration.

TPU provides a number of advantages for use as the composition for the flexible body 11. In FIGS. 2C and 2D, the flexible body 11 is an extruded TPU composition that can retain its shape after being manipulated. It is more flexible and thinner than conventional cannulas. FIG. 2C shows the flexible body 11 in a knotted configuration and FIG. 2D shows the flexible body 11 in a twisted configuration. Both the knotted and twisted configurations illustrate the flexibility of a flexible body 11 composed of TPU. The flexibility and resiliency of the flexible body 11 gives a better range of motion for the surgeon, as if there were operating percutaneously. The flexible body 11 is free to move anywhere and only limited on by the proximal dermal threaded body 13, which is fixed to the dermis. TPU is also resistant to cuts or other damage from sharp instruments, such as a shaver blade or bur. Further, the heat resistant qualities TPU mentioned briefly above allow for the passage of ablation instruments without deformation or other damage to the flexible body 11.

Figure 2E:
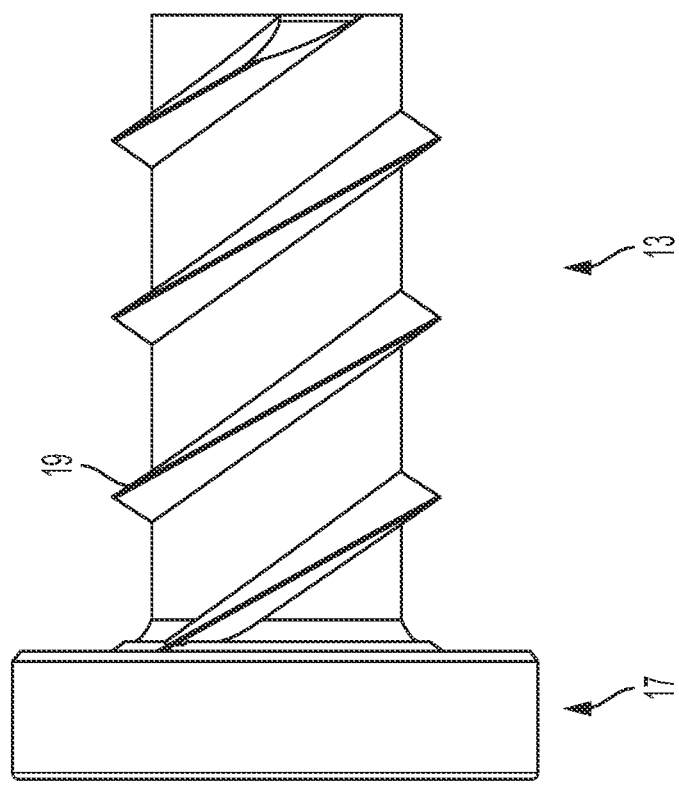
FIG. 2E is a side view schematic representation of a dermal threaded body and a seal, according to an embodiment.
Figure 2F:
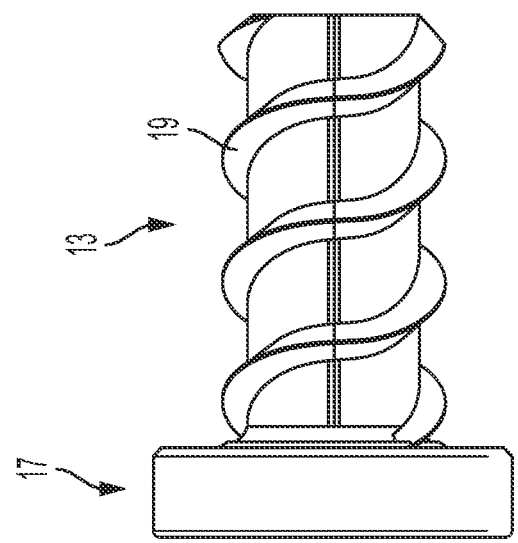
FIG. 2F is a top view schematic representation of a dermal threaded body and a seal, according to an embodiment.
Figure 2G:
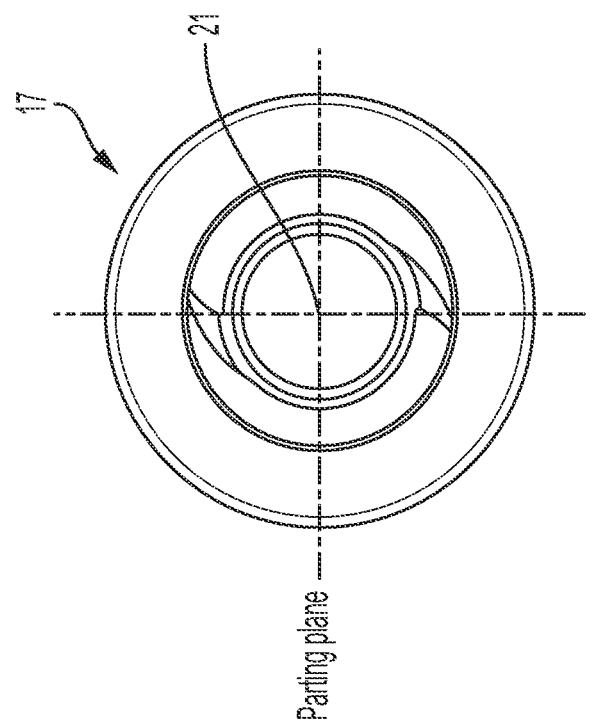
FIG. 2G is a front view schematic representation of a seal, according to an embodiment.
Figure 2I:
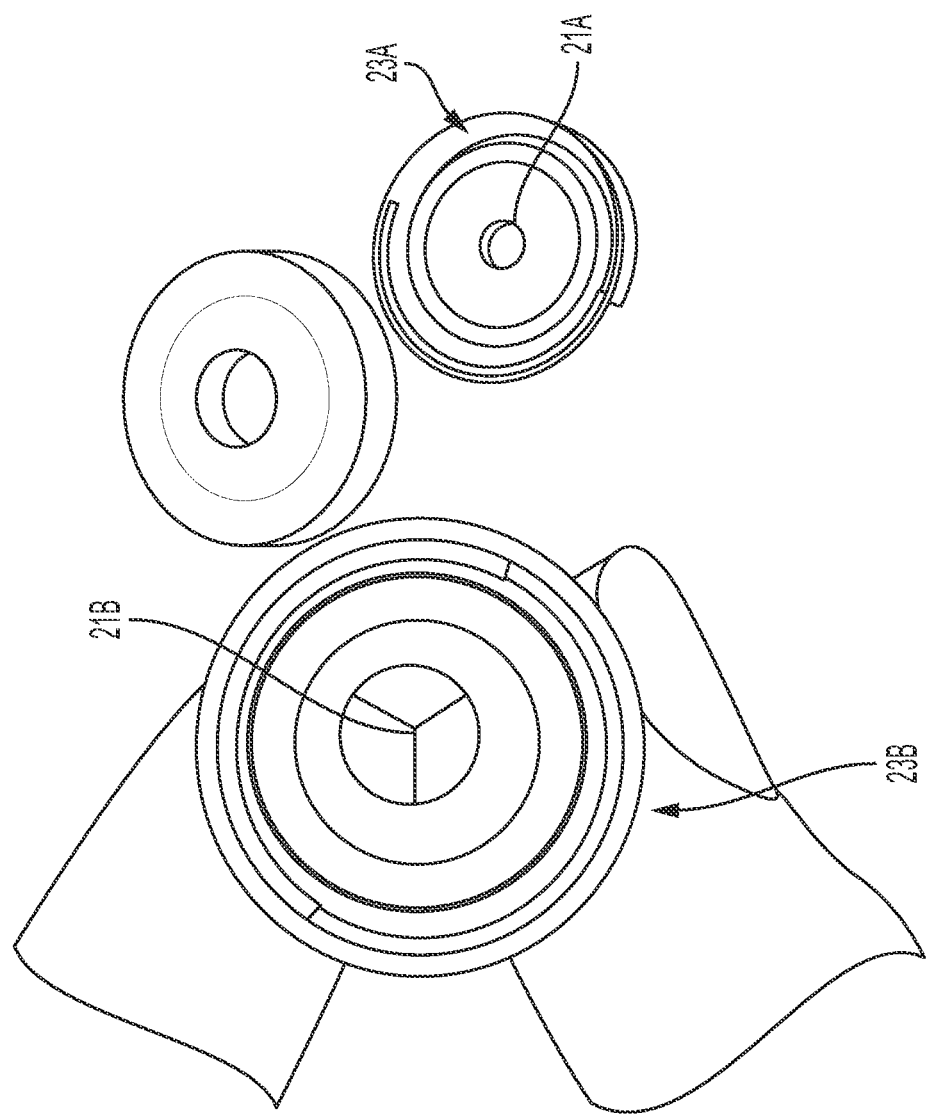
FIG. 2I is a front view schematic representation of a double seal, according to an embodiment.
Figure 2J:
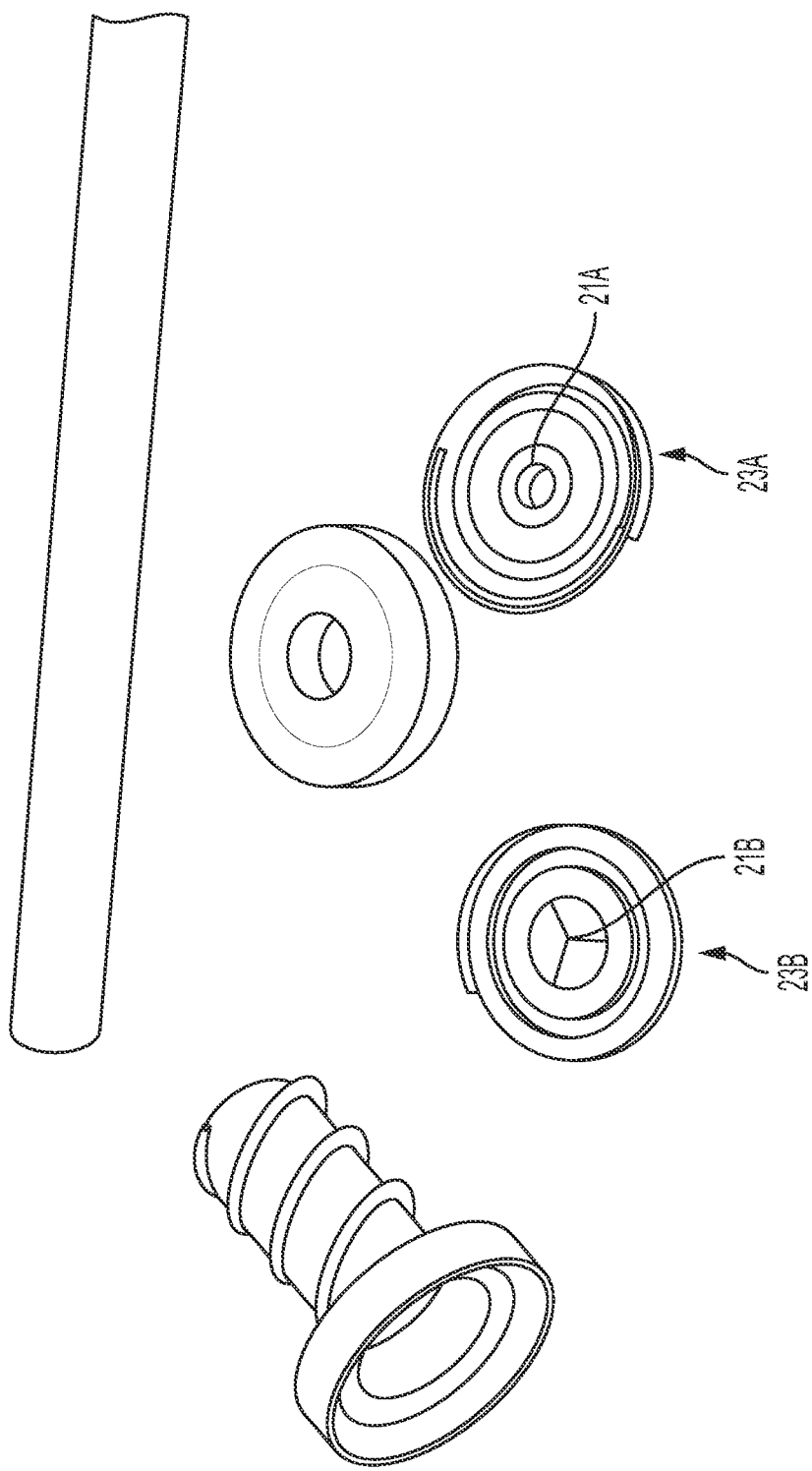
FIG. 2J is a perspective view schematic representation of a double seal, according to an embodiment.

Turning now to FIGS. 2E-2G, there are shown various views schematic representations of the dermal threaded body 13 and seal 17, according to an embodiment. In the depicted embodiment, the dermal threaded body 13 comprises external threads 19, as shown in FIGS. 2E-2F. FIG. 2G shows the seal 17 at the proximal end of the dermal threaded body 13. The seal 17 comprises an opening 21, which is as small as possible but also sized to accommodate all surgical devices for a surgical field or type of procedure (e.g., hip surgical devices). Although the seal 17 will prevent fluid leakage from the surgical site, it also prevents bubbles from migrating to the surgical site and blocking the view of a video scope. Exemplary embodiments of the seal 17 are shown in FIGS. 2H-2J. In the depicted embodiment, the seal 17 is a double seal. The double seal 17 includes a first seal 23A with a circular opening 21A and a second seal 23B "Mercedes" opening 21B (meaning an opening formed from three slits meeting at a central location), as shown in FIGS. 2I-2J.

Figure 3A:
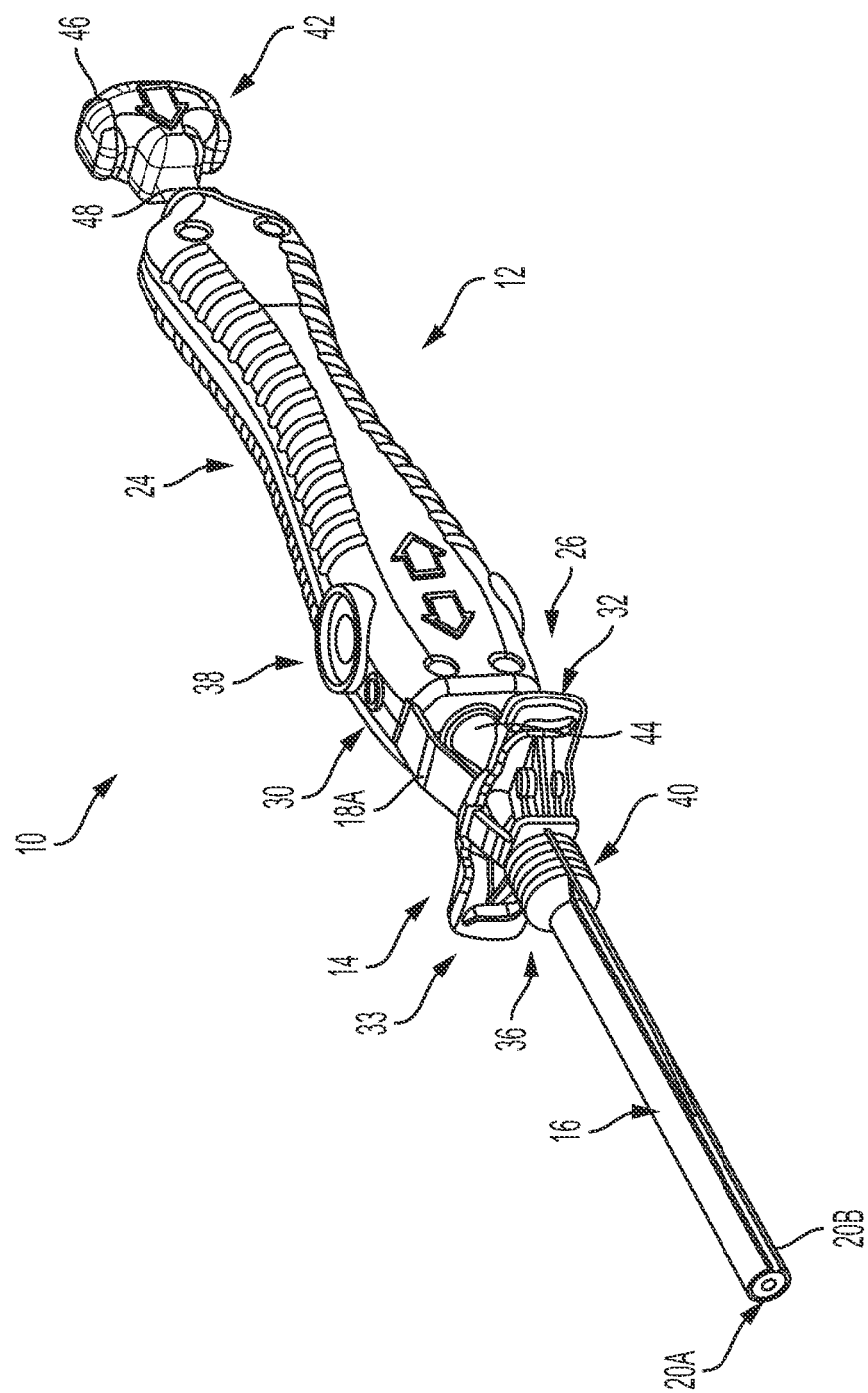
FIG. 3A is a perspective view schematic representation of a portal saver assembly, according to an embodiment.
Figure 3B:
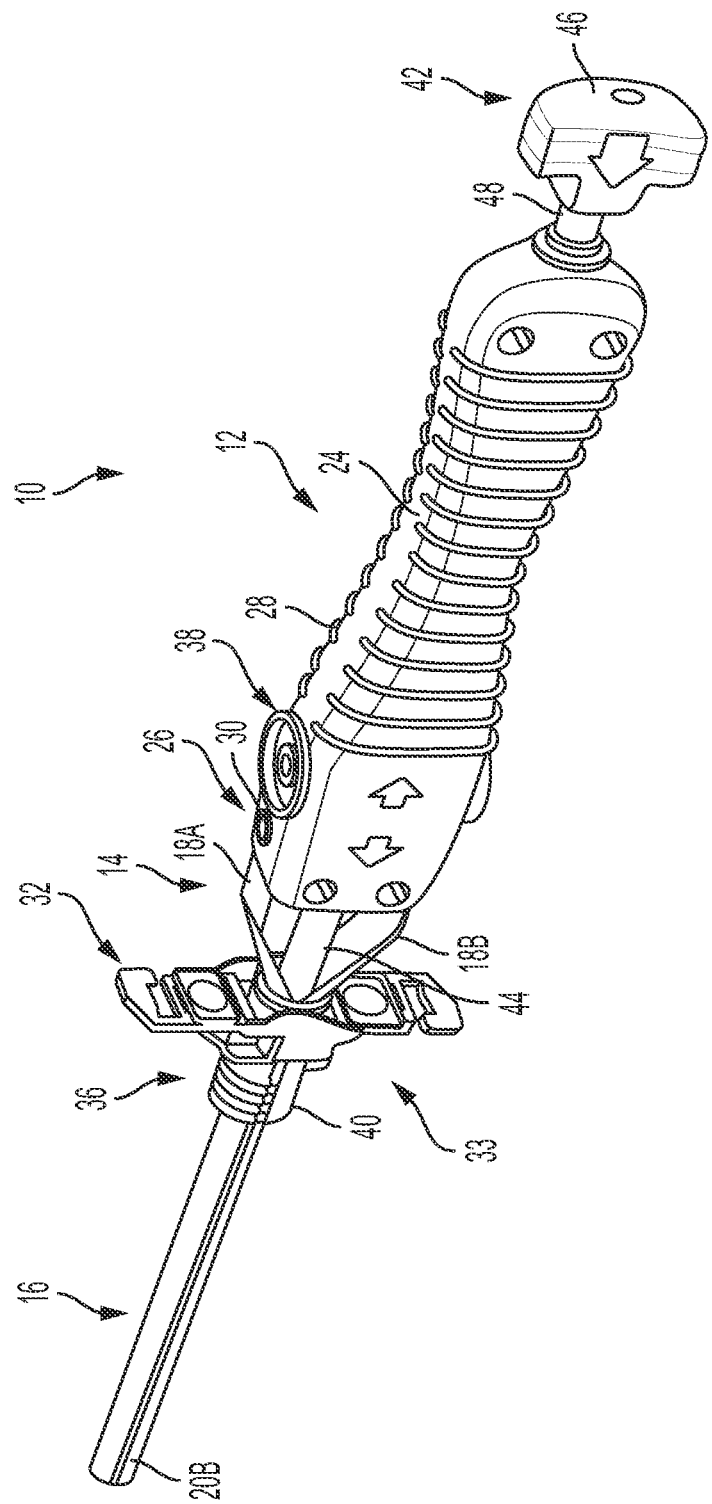
FIG. 3B is another perspective view schematic representation of a portal saver assembly, according to an embodiment.
Figure 4:
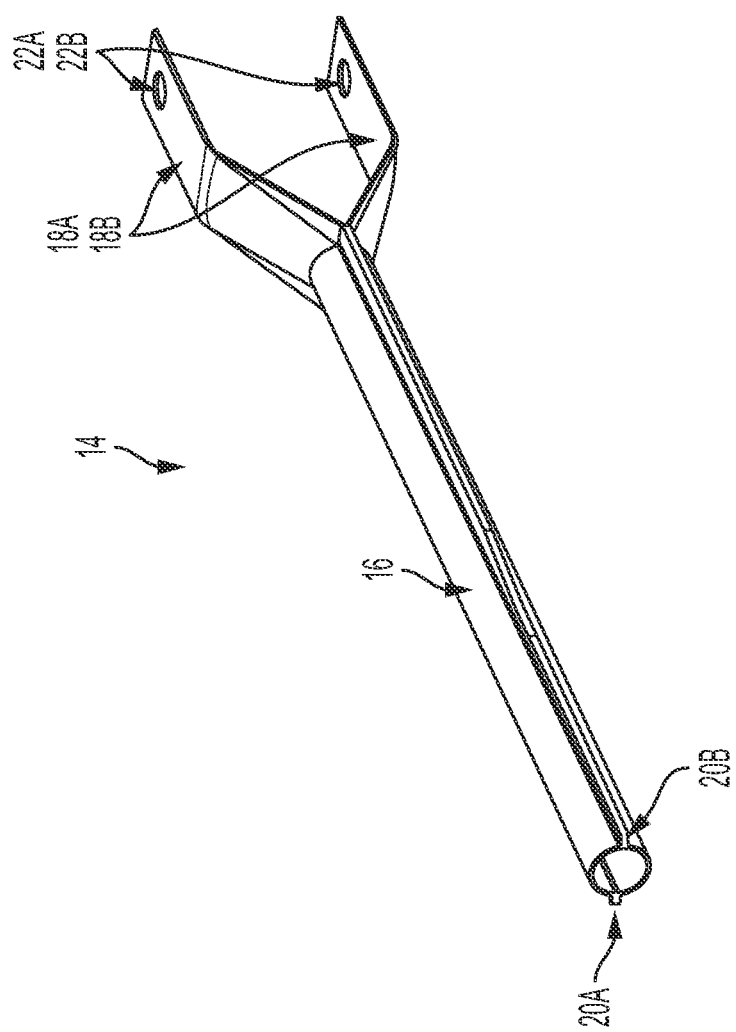
FIG. 4 is a perspective view schematic representation of a portal saver device, according to an alternative embodiment.

Referring now to FIGS. 3A-3B, there are shown perspective views schematic representations of a portal saver assembly 10, according to an embodiment. The portal saver assembly 10 comprises an obturator 12 removably connected to an alternative embodiment of the portal saver device 14. The portal saver device 14 includes a rigid, flexible body 16 extending to a pair of stirrups 18A, 18B, as shown in FIG. 4. In the embodiment depicted in FIG. 4, the flexible body 16 can be composed of flat sheet material and is welded, creating two seams 20A, 20B extending along a length of the flexible body 16. By nature, the flat sheet material composing the flexible body 16 is prone to collapsing back to a flat shape, which is beneficial for sealing and fluid management. In an alternative embodiment, the flat sheet material composing the flexible body 16 is imperfectly welded such that there is a frangible seal to peel apart the flexible body 16. In yet another embodiment, the flexible body 16 is extruded from the same flexible material (e.g., thermoplastic urethane ("TPU")) with no welded seams so that the flexible body 16 maintains a relaxed state (as shown in FIGS. 2A-2D).

As also shown in FIG. 4, the stirrups 18A, 18B of the portal saver device 14 extend proximally from the flexible body 16 such that the stirrups 18A, 18B are spaced and approximately parallel. In the depicted embodiment, the stirrups 18A, 18B each have an aperture 22A, 22B extending therethrough and the apertures 22A, 22B are aligned. In an alternative embodiment, the portal saver device 14 does not have stirrups, meaning that the flexible body 16 is connected to the obturator 12 directly. In yet another embodiment, the flexible body 16 does not extend to stirrups 18A, 18B, but instead has an exterior threaded portion adjacent a tubular end cap.

Referring back to FIGS. 3A-3B, as briefly mentioned above, the portal saver device 14 is connected to the obturator 12. Specifically, in the depicted embodiment, the obturator 12 comprises an obturator body 24 and the stirrups 18A, 18B extend into or onto the obturator body 24, while the flexible body 16 extends from a distal end 26 of the obturator body 24. The obturator body 24 in FIGS. 3A-3B is ergonomically shaped with spaced ridges 28 to aid in providing a secure grip for the surgeon (or any other user). Near or at the distal end 26 of the obturator body 24, a holding pin 30 (or any other conventional connector) extends through the obturator body 24 and through an aperture 20A of a stirrup 18A within the obturator body 24. A second holding pin 30 may also extend through the obturator body 24 and through the other aperture 20B on the other stirrup 18B within the obturator body 24. The holding pins 30 secure the stirrups 18A, 18B in place within the obturator body 24. The portal saver assembly 10 additionally comprises a stirrup release actuator 38. In the depicted embodiment, the stirrup release actuator 38 is a push button. Depressing or otherwise activating the stirrup release actuator 38 releases the portal saver device 14 from obturator body 24.

Still referring to FIGS. 3A-3B, the portal saver assembly 10 includes a distal rigid body 33. As shown, the rigid body 33 is secured around the portal saver device 14. In the depicted embodiment, the rigid body 33 is connected at a proximal end 36 of the flexible body 16. The rigid body 33 comprises a telescoping assembly 32, which is movable along the flexible body 16. The telescoping assembly 32 comprises one or more blades 34 (FIG. 8) for axial slitting of the flexible body 16 to reduce the effective length of the portal saver assembly 10. As also shown in FIGS. 3A-3B, the rigid body 33 also comprises exterior barbs 40 for fixation to the patient. In the depicted embodiment, the barbs 40 are adjacent and distal to the telescoping assembly 32.

Figure 5:
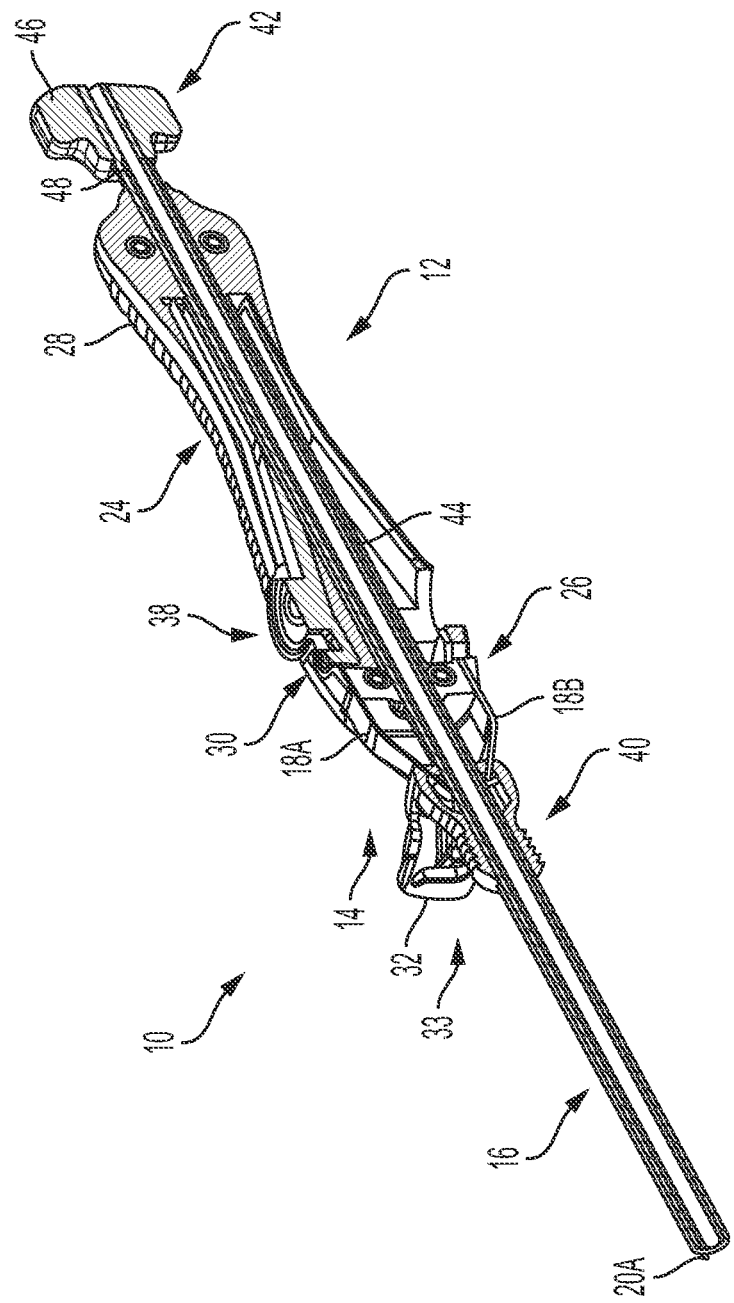
FIG. 5 is a perspective section view schematic representation of the portal saver assembly, according to an embodiment.

The portal saver assembly 10 in FIGS. 3A-3B also includes an obturator shaft expander 42 which is movable within the obturator 12 and the flexible body 16. Turning now to FIG. 5, there is shown a perspective sectional view schematic representation of the portal saver assembly 10, according to an embodiment. In the depicted embodiment, the shaft expander 42 is movable within a cannulated outer obturator tube 44 within the obturator body 24. As shown in FIG. 5, the outer obturator tube 44 extends through to obturator body 24, creating a channel within the obturator body 24 to receive the shaft expander 42.

Figure 7:
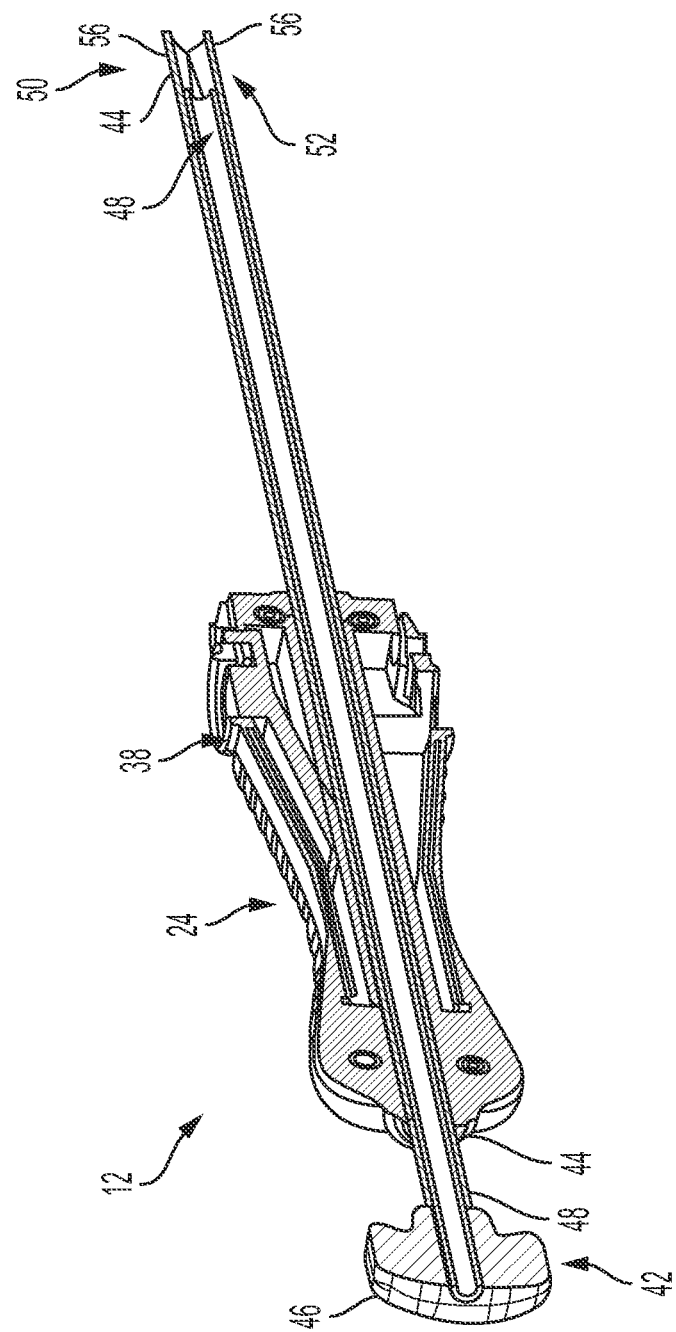
FIG. 7 is a perspective side section view schematic representation of the portal saver assembly in the first configuration, according to an embodiment.

The shaft expander 42 comprises a proximal handpiece 46 connected to cannulated inner obturator tube 48. The inner obturator tube 48 is sized and configured to slide within the channel of the cannulated outer obturator tube 44. In addition, the inner obturator tube 48 extends through the handpiece 46 such that an instrument can be inserted through the handpiece 46, the inner obturator tube 48, and out of the outer obturator tube 44 (FIG. 7). When the portal saver device 14 is connected to the obturator 12, as shown in FIG. 5, the inner obturator tube 48 is extendable through the outer obturator tube 44 and the flexible body 16 of the portal saver device 14.

Figure 6:
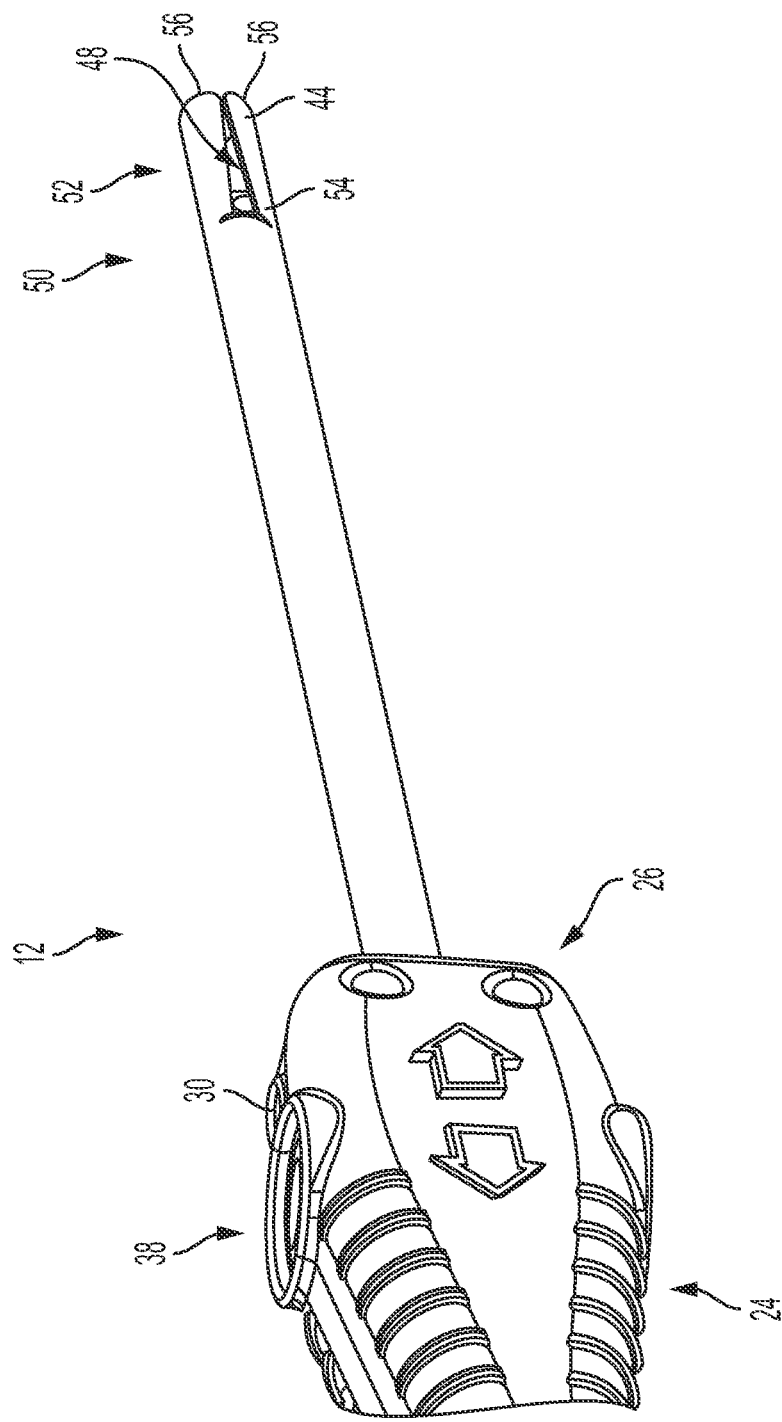
FIG. 6 is a side section view schematic representation of the distal tip of the portal saver assembly in a first configuration, according to an embodiment.

Turning now to FIG. 6, there is shown a close-up perspective view schematic representation of the distal tip 50 of the portal saver assembly 10, according to an embodiment. As shown in the depicted embodiment, the distal tip 50 comprises a duck bill portion 52 of the outer obturator tube 44. The duck bill portion 52 includes a pair of arms or prongs 56 (which can include additional arm or prong portions, or can in some embodiments can include one arm) formed by a recess (e.g., triangular or prism-shaped) in the outer obturator tube 44 that narrows toward the distal tip 50 of the outer obturator tube 44 (or portal saver assembly 10). The duck bill portion 52 opens when an actuator (e.g., small post) 54 on the inner obturator tube 48 is advanced toward the distal tip 50 of the outer obturator tube 44. As the small post 54 has not been advanced toward the distal tip 50 in FIG. 6, the arms 56 of the duck bill portion 52 are collapsed (i.e., in a first configuration).

Figure 8:
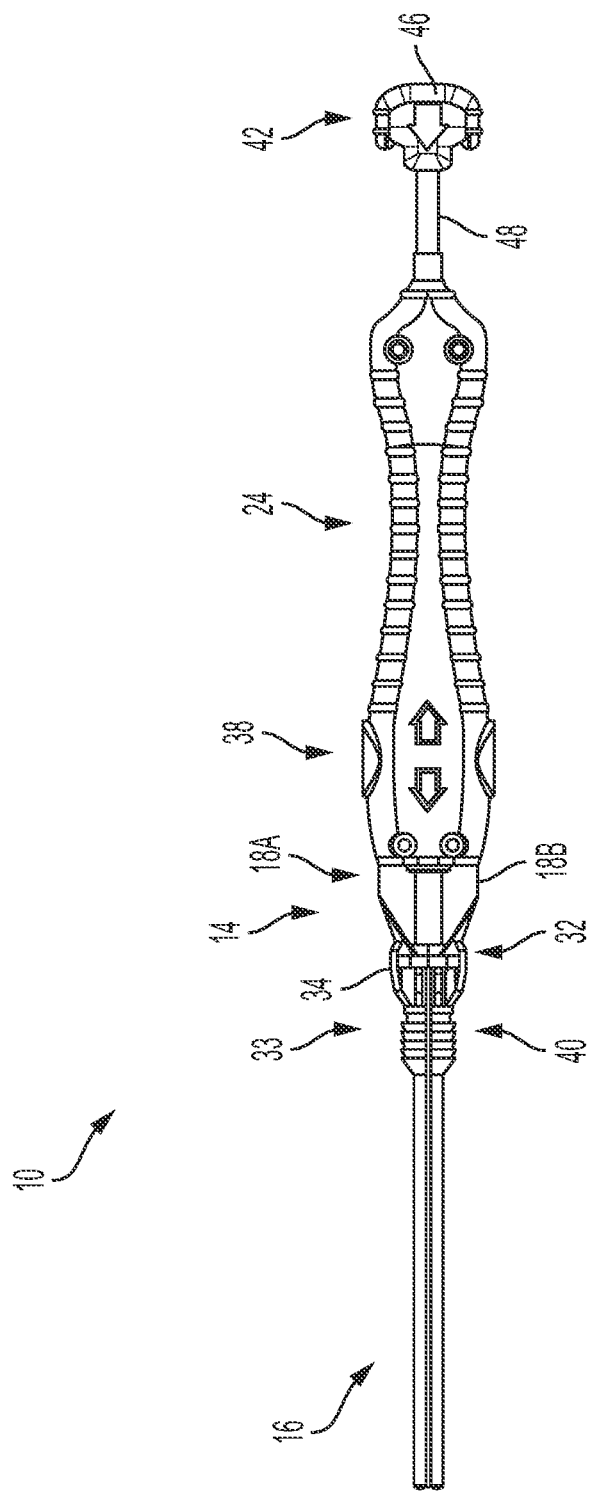
FIG. 8 is a side view schematic representation of the portal saver assembly in the first configuration, according to an embodiment.
Figure 9:
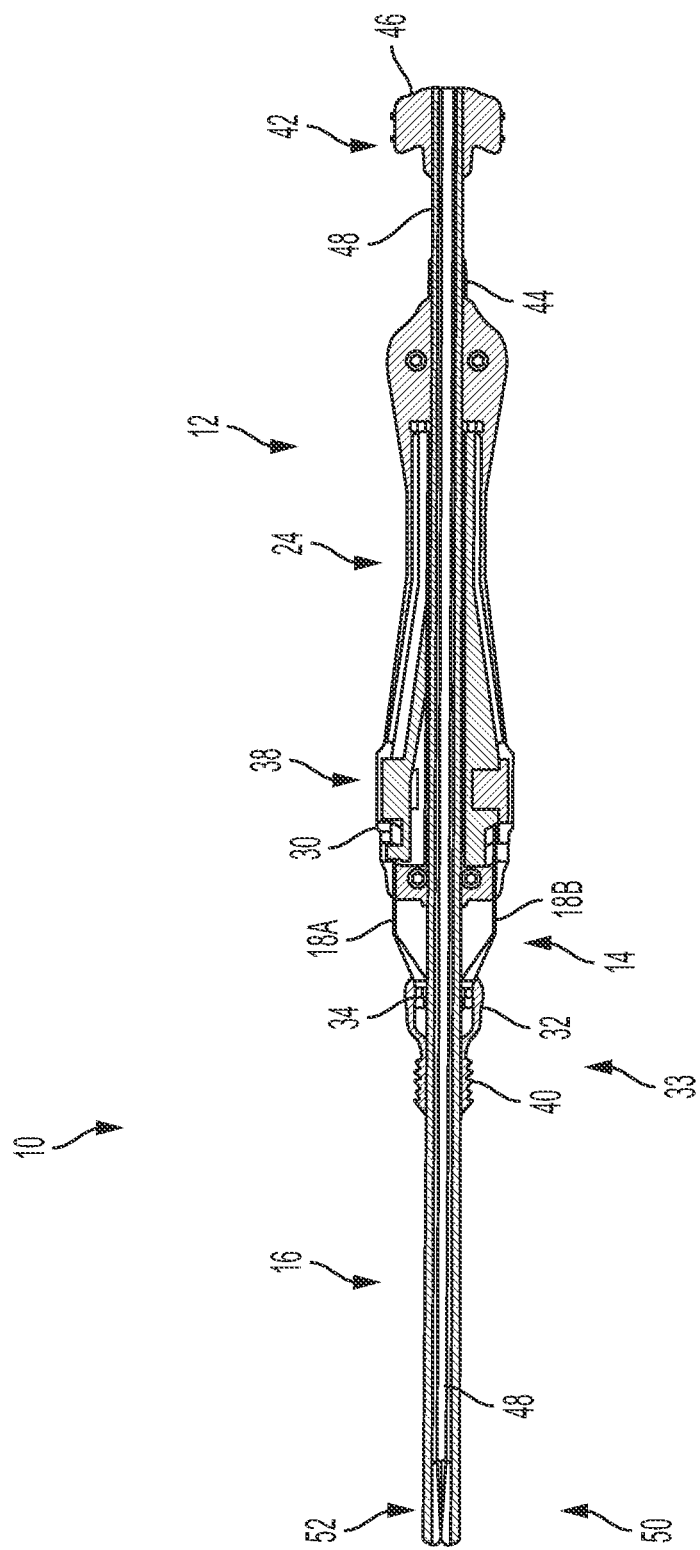
FIG. 9 is a side section view schematic representation of the portal saver assembly in the first configuration, according to an embodiment.

Turning now to FIGS. 7-9, there is shown perspective and side section views schematic representations of the portal saver assembly 10 in the first configuration, according to an embodiment. Referring now to FIG. 7, there is shown a perspective side section view schematic representation of the portal saver assembly 10 in the first configuration, according to an embodiment. Specifically, FIG. 7 shows the obturator 12 with the portal saver device 14 removed (or unattached). In the depicted embodiment, the shaft expander 42 is in a first position relative to the obturator body 12. When the shaft expander 42 is in the first position, the inner obturator tube 48 is at least partially proximally retracted within the outer obturator tube 44. As a result, the duck bill portion 52 is collapsed in the first configuration, as shown in FIG. 7.

FIGS. 8 and 9 show a side view schematic representation and side section view schematic representation, respectively, of the portal saver assembly 10 in the first configuration, according to an embodiment. In both FIGS. 8 and 9, the portal saver device 14 is connected to the obturator 12. As shown, when the shaft expander 42 is retracted to the first position, the duck bill portion 52 is collapsed in the first configuration. Although the outer obturator tube 44 is collapsed, the flexible body 16 of the portal saver device 14 is not, as shown in FIG. 8.

Figure 10:
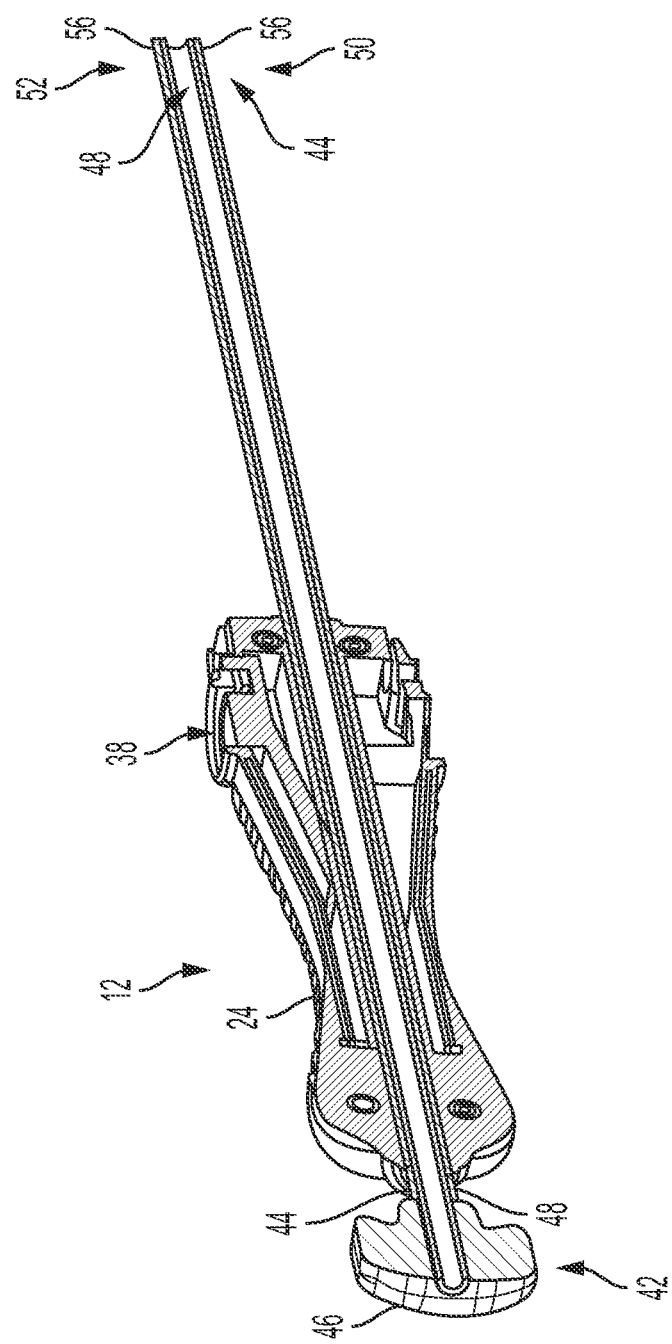
FIG. 10 is a perspective section view schematic representation of the portal saver assembly in a second configuration, according to an embodiment.
Figure 11:
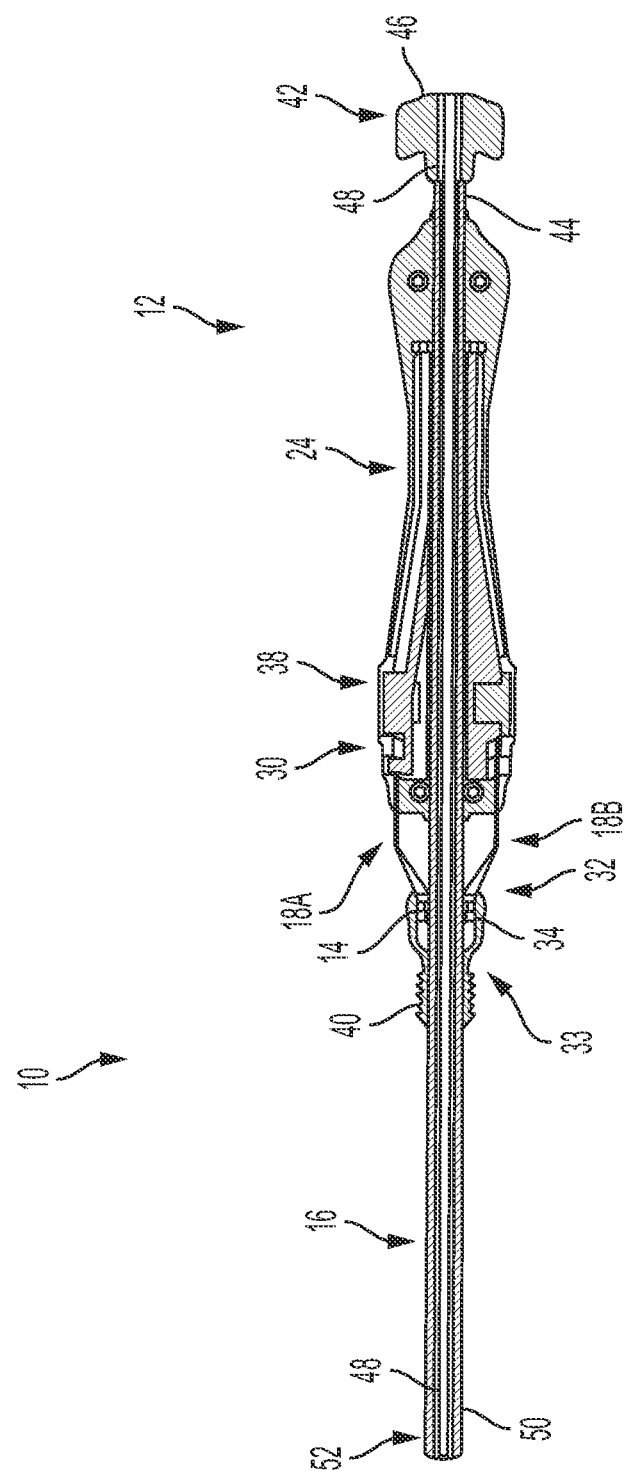
FIG. 11 is a side section view schematic representation of the portal saver assembly in a second configuration, according to an embodiment.

Referring now to FIGS. 10 and 11, there is shown a perspective section view schematic representation and side section view schematic representation, respectively, of the portal saver assembly 10 in a second configuration, according to an embodiment. FIG. 10 shows the obturator 12 with the portal saver device 14 removed (or unattached). When the shaft expander 42 is moved distally or fully advanced toward the obturator body 24 to a second position, the inner obturator tube 48 extends distally into the duck bill portion 52 of the outer obturator tube 44. Specifically, the small post 54 on the inner obturator tube 48 is advanced toward the distal tip 50 of the outer obturator tube 44, forcing the arms 56 of the duck bill portion 52 to open to an expanded, second configuration, as shown in FIGS. 10-11. Thus, the small post 54 functions to increase an inner diameter of the outer obturator tube 44.

FIG. 11 shows the duck bill portion 52 in the expanded, second configuration when the portal saver device 14 is attached to the obturator 12. When the duck bill portion 52 is opened to the second configuration, frictional force is applied to the flexible body 16 near the distal tip 50. The friction of the duck bill portion 52 overcomes the friction of the tissue of the patient as the flexible body 16 is inserted down into the joint (i.e., surgical site), which in turn prevents the flexible body 16 from slipping or rolling up. The expanded or increased inner diameter of the outer obturator tube 44 in the second configuration also allows for flexibility of instruments passing through the portal saver assembly 10. Accordingly, instruments with a relatively larger diameter or instruments with a bend can be passed through the portal saver assembly 10.

Although a duck bill portion 52 is shown, any other dilation assembly can be used that applies radially outward force to the outer obturator tube 44. In an alternative embodiment, the dilating assembly is a bead instead of the small post 54. The inner obturator tube 48 extends past the duck bill portion 52 with a bead, forcing the outer obturator tube 44 to expand (via the arms 56). Other actuator or dilating assemblies are contemplated for alternative embodiments. For example, a small pocket on an exterior of distal tip 50 of the outer obturator tube 44 can be used. In another example, a solid rod can be used to displace the distal tip 50 of the outer obturator tube 44.

In order to use the portal saver assembly 10, the surgeon (or other user) can slide the portal saver assembly 10, in the first configuration into the hip joint. The portal saver assembly 10 is advanced medially into the patient until the distal tip 50 gains intra-ocular joint access. Then, the rigid body 33 is advanced distally down the flexible body 16 until it is fully engaged with the patient dermis. (The portal saver assembly 10 can be configured for the dermal openings used in most procedures, including a 16 mm dermal opening diameter). At this time, the proximal telescoping assembly 32 simultaneously cleaves (via the blade 34) the flexible body 16 while locking its position until the distal barbs 40 are sub-flush with the patient's dermis. The flexible body 16 is trimmed flush with the blade 34 of the proximal telescoping assembly 32.

In an alternative embodiment, the length of the flexible body 16 can be shortened by cutting it to a desired length. In such an embodiment, the flexible body 16 may have measurements or indicators (via printing or etching, for example) along the length of the flexible body 16. In yet another embodiment, the flexible body 16 may have perforations or other like grooves along its length for tearing to the desired length.

With the flexible body 16 trimmed to the desired length and the barbs 40 securing the rigid body 33 within the patient, the stirrup release actuator 38 on the obturator 12 is actuated and disengages the rigid body 33 and the cleaved flexible body 16. The obturator 12 is then removed. The obturator 12 can be reloaded with additional rigid bodies 33 and cannulated tubes 16 for the placement of additional intra-articular access portals on the patient. Now, with the rigid body 33 and flexible body 16 in place, all surgical instruments can gain intra-articular access through the flexible body 16 in lieu of dedicated access instruments. The rigid body 33 and flexible body 16 can be removed at the end of the procedure.

Figure 12:
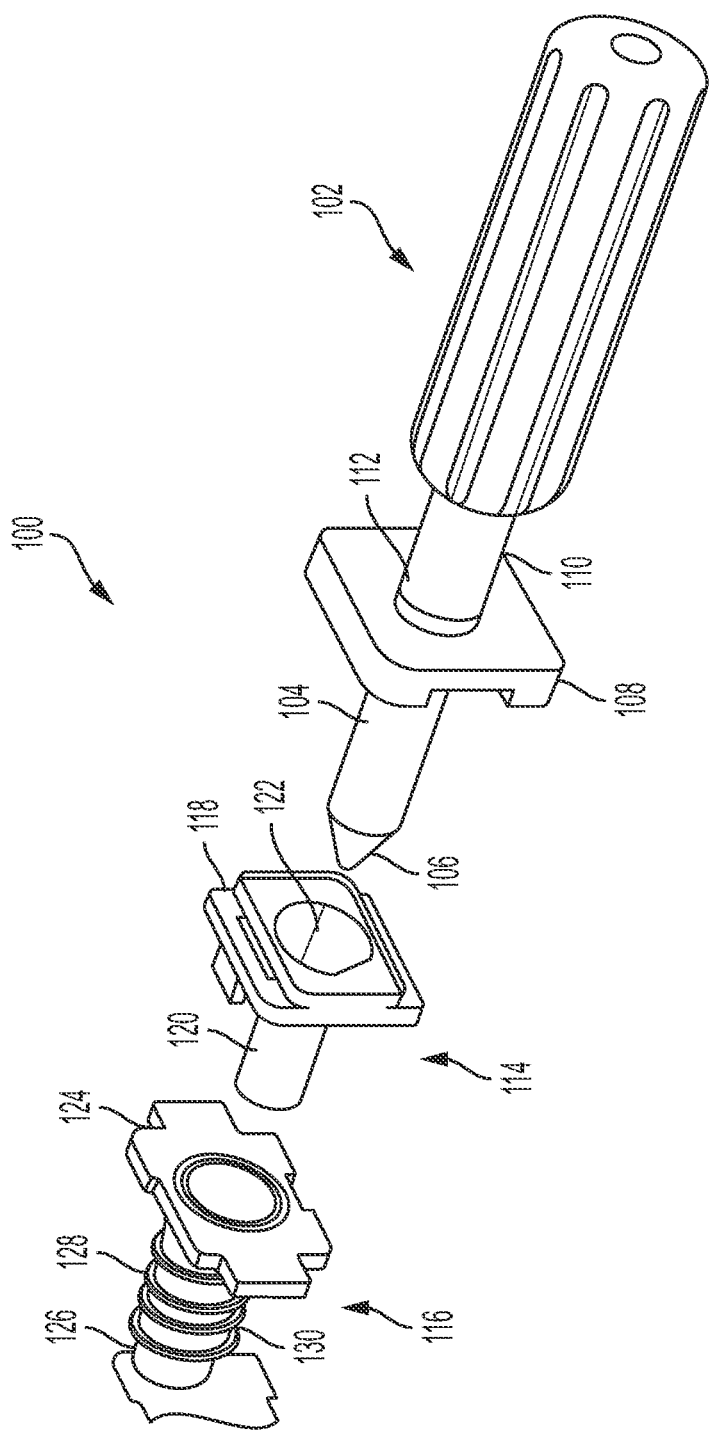
FIG. 12 is an exploded perspective view schematic representation of a portal saver assembly, according to an alternative embodiment.

Referring now to FIG. 12, there is shown an exploded perspective view schematic representation of a portal saver assembly 100, according to an alternative embodiment. In the depicted embodiment, the portal saver assembly 100 comprises a proximal obturator 102 with an outer obturator tube 104 extending therefrom. In an embodiment, the outer obturator tube 104 is composed of flat sheet material and is welded, creating two seams (not shown) extending along a length of the outer obturator tube 104. By nature, the flat sheet material composing the outer obturator tube 104 is prone to collapsing back to a flat shape, which is beneficial for sealing and fluid management.

As shown in FIG. 12, the outer obturator tube 104 terminates in a distal tip 106. The obturator 102 and the outer obturator tube 104 are cannulated such that they are configured to receive instruments therethrough. The outer obturator tube 104 additionally comprises a covering 108 which is connected to an exterior 110 of the outer obturator tube 104. As shown in FIG. 12, the covering 108 is rectangular (or square) with a central aperture 112 which is sized and configured to fit around and connect (or fix) to the outer obturator tube 104. In the depicted embodiment, the outer obturator tube 104 and the covering 108 are formed via molding such that the outer obturator tube 104 and covering 108 are made from the same piece of material.

Still referring to FIG. 12, the portal saver assembly 100 shown also includes an adjustable seal 114 and a dermal threaded body 116 for fixing the portal saver assembly 100 to the patient. The adjustable seal 114 is flexible and comprises a rectangular (or square) distal end 118 and an inner obturator tube 120 extending proximally therefrom. The inner obturator tube 120 is flexible such that it can be expanded to accommodate the outer obturator tube 104 and the instruments therein. The rectangular distal end 118 comprises an aperture 122 to receive the distal tip 106 of the outer obturator tube 104. The dermal threaded body 116 comprises a rectangular (or square) distal end 124 and a cannulated tube 126 extending proximally therefrom. The cannulated tube 126 has plurality of threads 128 on its exterior surface 130 which lock the dermal threaded body 116 (and the portal saver assembly 100) within the patient.

In use, the distal end 124 of the dermal threaded body 116 is configured to lock (via a snap connection other similar connection) into the distal end 118 of the adjustable seal 114 and the covering 108 around the outer obturator tube 104, securing the adjustable seal 114 between the dermal threaded body 116 and the covering 108. The portal saver assembly 100 is advanced into the incision site and the dermal threaded body 116 is rotated into the dermal layer. (The portal saver assembly 100 can be configured for the dermal openings used in most procedures, including a 15 mm dermal opening diameter). The threads 128 on the exterior surface 130 of the dermal threaded body 116 create a holding force in the dermal layer. The connection (e.g., snap connection) between the distal end 124 of the dermal threaded body 116 and the covering 108 around the outer obturator tube 104 can be broken (e.g., unsnapped) to remove the obturator 102 from the incision site. The holding force created by the threads 128 of the dermal threaded body 116 prevents cannulas, instruments, and other tools from falling out of the portal. When the surgical procedure is complete, the adjustable seal 114 can be disconnected (e.g., unsnapped) and the dermal threaded body 116 can be unscrewed or otherwise removed and then passed back through the original incision for easy removal without causing additional trauma or scarring to the skin or dermis of the patient.

Figure 13:
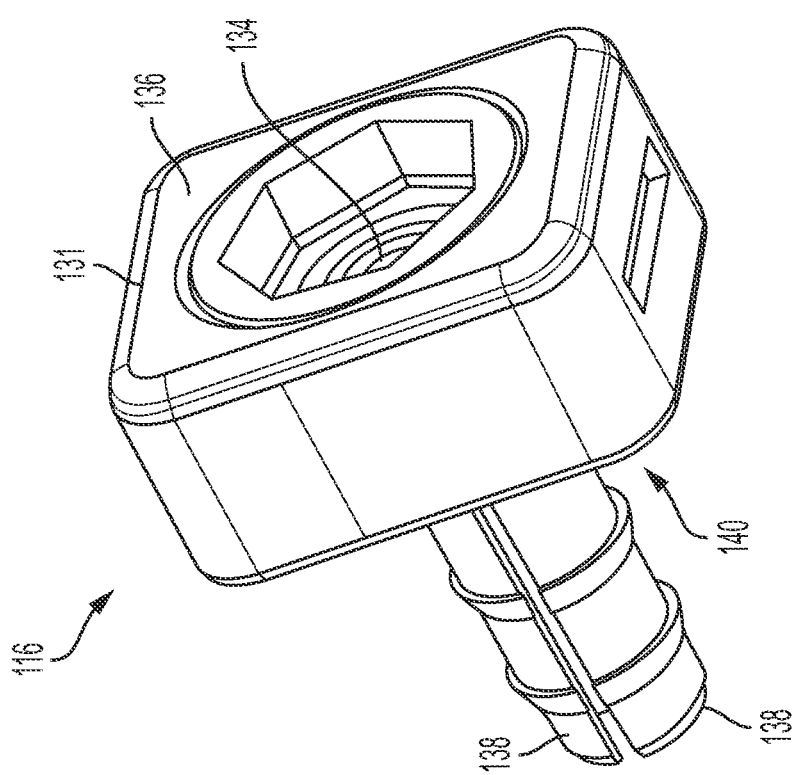
FIG. 13 is a perspective view schematic representation of a distal body, according to an alternative embodiment.
Figure 14:
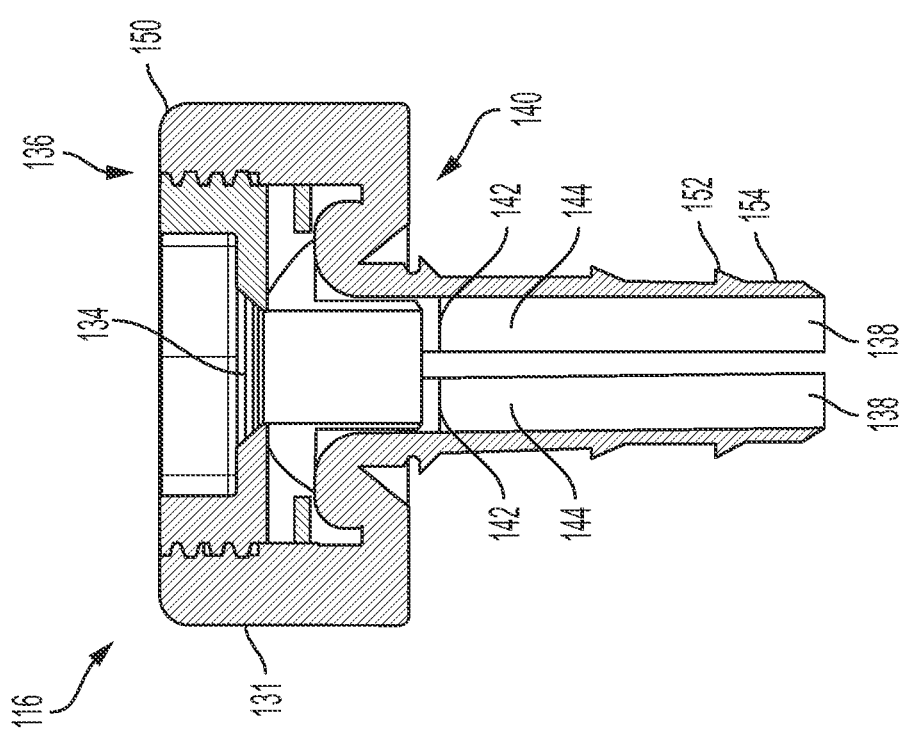
FIG. 14 is a side section view schematic representation of a distal body in a first configuration, according to an alternative embodiment.
Figure 15:
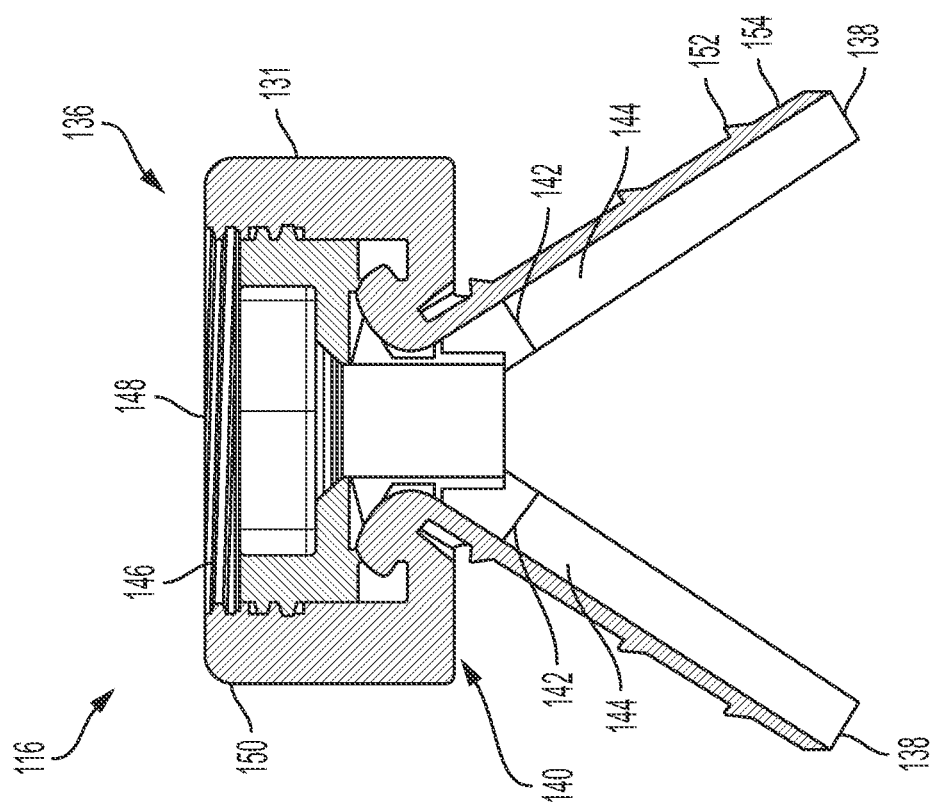
FIG. 15 is a side section view schematic representation of a distal body in a second configuration, according to an alternative embodiment.

Referring now to FIGS. 13-15, there are shown various views schematic representations of the distal (unthreaded) body 116, according to an alternative embodiment. FIG. 13 shows a perspective view schematic representation of the distal body 116. The distal body 116 comprises a cup-like top portion 131. In the depicted embodiment, the top portion 131 has a rectangular (or square) cross-section. The top portion 131 comprises a threaded interior bore 134 on a first end 136 and at least two petals 138 extending from the second end 140 of the top portion 131. The petals 138 are arms or prongs which are movable in relation to each other from a first configuration to a second configuration. Although two petals 138 are shown in FIG. 13, additional petals 138 can be utilized.

FIG. 14 shows the petals 138 in the first configuration. In the first configuration, the petals 138 are approximately parallel to each other such that they extend in the same direction. As shown, each petal 138 has raised portions 142 (e.g., ridges or other protrusions) on an interior surface 144 of the petal 138. If force is applied to the raised portions 140 in the distal direction, the petals 138 move from the first configuration to the second configuration. In an embodiment, the raised portions 140 are pushed downward (in the distal direction) by a disc 146 with male threads 148 configured to mate with the female threads 150 of the interior bore 131. As the disc 146 advances downward (in the distal direction) through the interior bore 134, it presses or otherwise applies pressure to the raise portions 142 causing the petals 138 to expand (or pivot about a pivot point) to the second configuration shown in FIG. 15. In other words, the disc 146 pushes the petals 138 from a relatively parallel position in the first configuration to an angled position in the second configuration.

In use, the distal body 116 is in the first configuration with the petals 138 approximately parallel, making the distal body 116 small in size. The small size allows the distal body 116 to enter the human body through a smaller incision as compared to those for other cannulas with coarse aggressive exterior threads. The distal body 116 is inserted to a depth within the incision where the top portion 131 is in contact with the skin of the patient. Thereafter, the disc 146 is threaded or advanced into the interior bore 134 of the top portion 131. As a result, the disc 146 pushes the petals 138 radially outward to the expanded, second configuration. The expansion of the petals 138 under the dermal layer of the patient creates a holding force in the dermal layer. The holding force prevents the cannula from falling out of the portal. When the surgical procedure is complete, the disc 146 can be unscrewed or otherwise removed, causing the petals 138 to retract and move toward each other to the first configuration. The distal body 116 can then be removed or passed back through the original incision for easy cannula removal without causing additional trauma or scarring to the skin or dermis of the patient.

In an alternative embodiment, each petal 138 has a "living hinge" as a means to connect the petal 138 to the top portion 131 instead of a mechanical pivoting point (as in FIGS. 13-15). Further, FIGS. 13-15 show petals 138 having a half-cylinder section; however, any conceivable shape, length, and cross-section can be used. In the depicted embodiment, each petal 138 has a small barb 152 on an exterior surface 154. However, in other embodiments, any number of barbs 152 or other features can be used to increase the hold of the petal 138 on the tissue.

Figure 16:
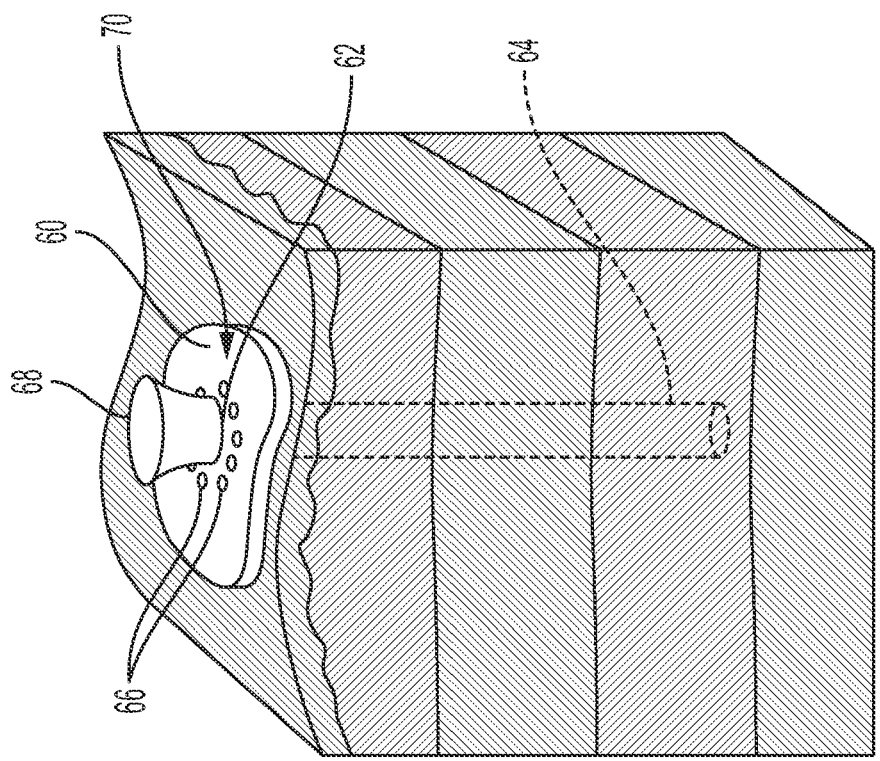
FIG. 16 is a perspective diagrammatic view of a dermal fixation device, according to an embodiment.
Figure 17:
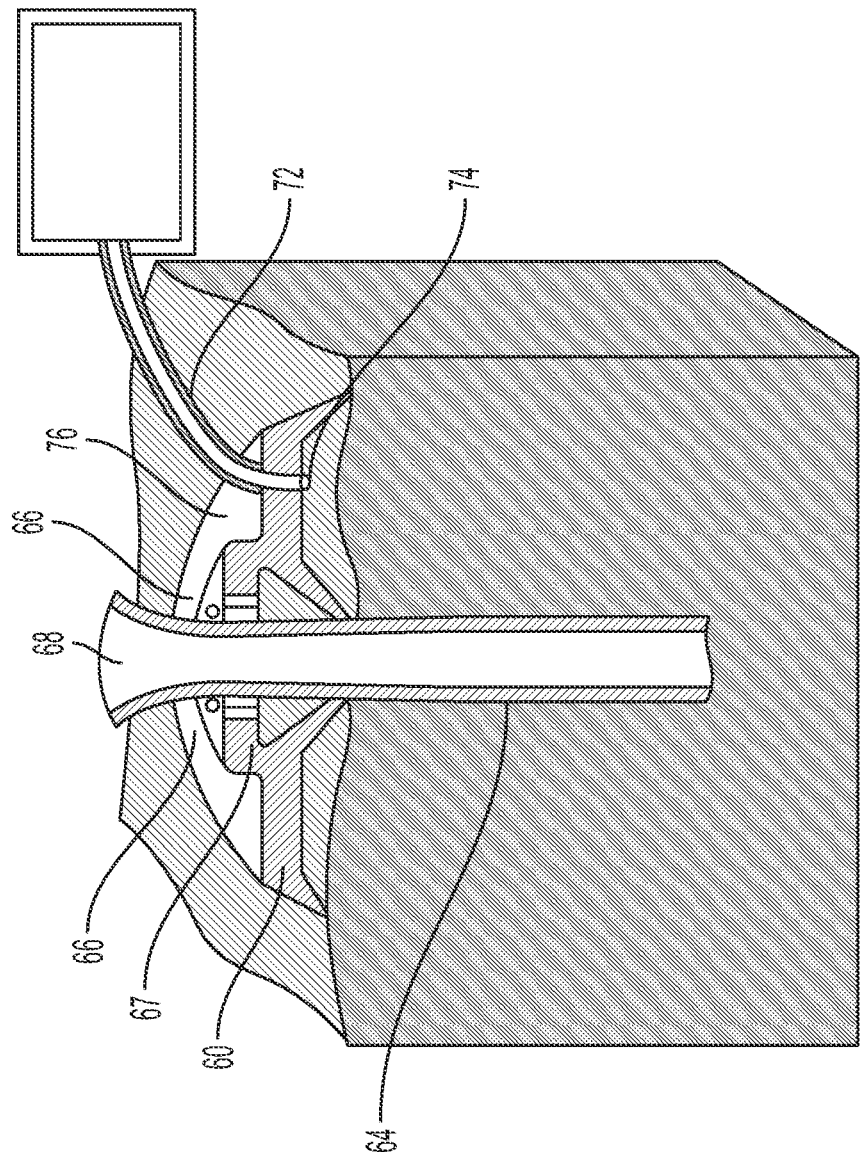
FIG. 17 is a perspective diagrammatic view of a dermal fixation device, according to an alternative embodiment.

Referring now to FIGS. 16-17, there are shown dermal fixation devices 60, according to alternative embodiments. The dermal fixation devices 60 in FIGS. 16-17 can be used as an alternative to exterior mechanical threads on the dermal threaded body 116 (FIG. 12) or any other mechanism threads for fixation of an access tool into the skin or dermis of the patient described herein. FIGS. 16-17 provide dermal fixation devices 60 that do not require any such external mechanical threads. The dermal fixation device 60 in FIG. 16 is an adhesive disc. The disc 60 comprises a central aperture 62 such that a cannula 64 can be placed therethrough, as shown in FIG. 16. In an embodiment, the disc 60 is flexible to conform to the shape of the patient's skin. In other embodiments, the disc 60 is semi-rigid or rigid. While the disc 60 in the depicted embodiment is circular, the disc 60 may be non-circular. Further, multiple discs 60 or a network of discs 60 may be utilized with a plurality of instruments and cannulas 64 to form a surgical system.

As shown in FIG. 16, the disc 60 comprises a plurality of weep holes 66 (i.e., apertures) adjacent the central aperture 62. In the depicted embodiment, the plurality of weep holes 66 surround the central aperture 62. Ideally, the plurality of weep holes 66 are above the surgical incision to allow fluid leaking from the incision to exit out from under the disc 60 through a controlled pathway that does not disrupt the adhesive/skin interface. In other words, the weep holes 66 allow for the release of fluid that may otherwise lift the adhesive disc 60 away from the skin. Although weep holes 66 are shown in FIG. 16, the disc 60 may be utilized without weep holes 66.

In an embodiment, prior to use of the disc 60 at the surgical incision, the cannula 64 can be attached to the disc 60. In one example, the disc 60 may comprise a layer of hook and loop fasteners (or any similar fasteners) configured to attach to complimentary hook and loop fasteners on the cannula 64. Using the hook and loop fasteners, the cannula 64 can be temporarily (i.e., removably) attached to the disc 60. Any other surgical resource may also comprise complimentary hook and loop fasteners for this purpose. With the cannula 64 attached to the disc 60, the disc 60 is likely to remain in-place throughout the duration of the surgical procedure. In addition, the user can selectively install or un-install the cannula 64 (or other surgical resource) at-will without disrupting the adhesive/skin interface during the surgical procedure.

In another embodiment, the adhesive on the disc 60 is covered with a protective covering (e.g., a peel-away liner) to protect the adhesive film until it is needed. Further, once the cannula 64 is inserted into the surgical incision, the area around the incision can be cleaned to improve adhesion of the disc 60 to the patient's skin before the protective covering is removed.

In an embodiment, as shown in FIG. 16, a funnel-shaped lead-in 68 can be used on a distal end 70 of the cannula 64 for the easy insertion of surgical instruments. The flexibility of the disc 60 allows for great flexibility and freedom of motion for surgical instruments. As there are no screw threads or barbs in the disc 60 shown in FIG. 16, the disc 60 has a small enough diameter to easily pass through a small incision, minimizing scarring and trauma to the region surrounding the incision. To remove the disc 60, it is pulled away from the incision site, starting at an outer edge of the disc 60 and slowly lifting it to peel it away. Once the disc 60 is separated from the incision site, the cannula 64 (preferably with no barbs or threads) can be easily and smoothly removed with minimal trauma.

Turning now to FIG. 17, the dermal fixation device 60 is a suction cup. In the depicted embodiment, the suction cup 60 is annular-shaped with a central aperture 62 to receive and attach to a cannula 64. The cannula 64 is connected to the suction cup 60 such that the cannula 64 can articulate and pivot (via an articulating attachment 67) with respect to the suction cup 60. In the depicted embodiment, the suction cup 60 is flexible in order to conform to the contours of the patient's skin for a secure seal. In other embodiments, the suction cup 60 is semi-rigid or rigid. While the suction cup 60 in the depicted embodiment is annular, the suction cup 60 may be non-round or non-annular. Further, multiple suction cups 60 or a network of suction cups 60 may be utilized with a plurality of instruments and cannulas 64 to form a surgical system.

The suction cup 60 may also comprise a plurality of weep holes 66 (i.e., apertures) adjacent or surrounding the central aperture 62. The weep holes 66 are above the surgical incision to allow fluid leaking from the incision to exit out from under the suction cup 60 so that the fluid does not disrupt the suction cup/skin interface. Although weep holes 66 are shown in FIG. 17, the suction cup 60 may be utilized without weep holes 66.

In an embodiment, prior to use of the suction cup 60 at the surgical incision, the cannula 64 can be attached to the suction cup 60. In one example, the suction cup 60 may comprise a layer of hook and loop fasteners (or any similar fasteners) configured to attach to complimentary hook and loop fasteners on the cannula 64. Using the hook and loop fasteners, the cannula 64 can be temporarily (i.e., removably) attached to the suction cup 60. Any other surgical resource may also comprise complimentary hook and loop fasteners for this purpose. With the cannula 64 attached to the suction cup 60, the suction cup 60 is likely to remain in-place throughout the duration of the surgical procedure. In addition, the user can selectively install or un-install the cannula 64 (or other surgical resource) at-will without disrupting the suction cup/skin interface during the surgical procedure.

In use, the cannula 64 is inserted into the patient and the area surrounding the incision is cleaned to improve the suction cup/skin interface. Next, the suction cup 60 is brought into contact with the patient's skin at the incision site. A vacuum 72 from a regulated vacuum supply is applied to the annular suction cup 60 via a portal 74 on the suction cup 60. In the depicted embodiment, the portal 74 is on a proximal side 76 of the suction cup 60; however, the portal 74 may be placed at any accessible location on the suction cup 60. The suction of the vacuum 72 causes the suction cup 60 to adhere to the skin, causing the cannula 64 to be become fixated to the patient's skin.

As with the dermal fixation device 60 described above and shown in FIG. 16, a funnel-shaped lead-in 68 can be used on a distal end 70 of the cannula 64 for the easy insertion of surgical instruments. The flexibility of the articulating mounting point allows for great flexibility and freedom of motion for surgical instruments. As there are no screw threads or barbs in the suction cup 60 shown in FIG. 17, the suction cup 60 has a small enough diameter to easily pass through a small incision, minimizing scarring and trauma to the region surrounding the incision. To remove the suction cup 60, the vacuum supply is turned off and the suction cup 60 is lifted away from the incision site. Once the suction cup 60 is separated from the incision site, the cannula 64 (preferably with no barbs or threads) can be easily and smoothly removed with minimal trauma.

Figure 18:
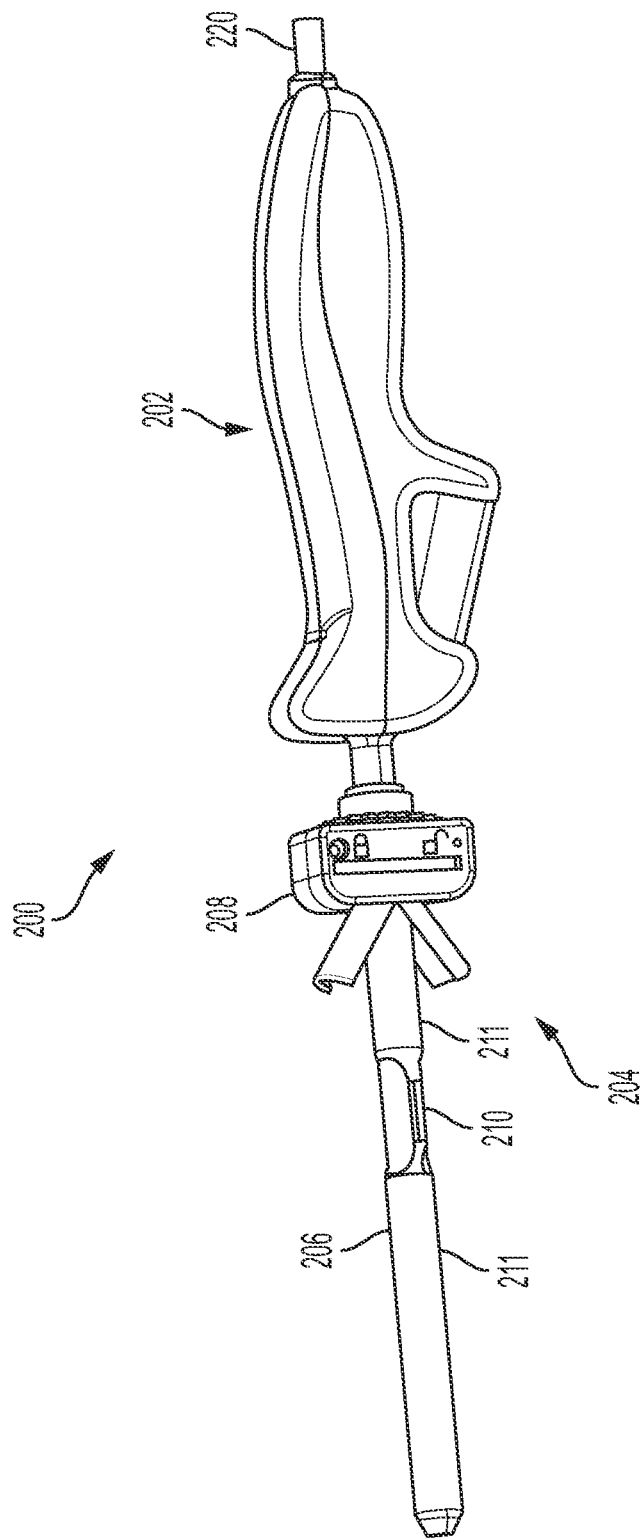
FIG. 18 is a side perspective view schematic representation of a portal saver assembly, according to an alternative embodiment.
Figure 19:
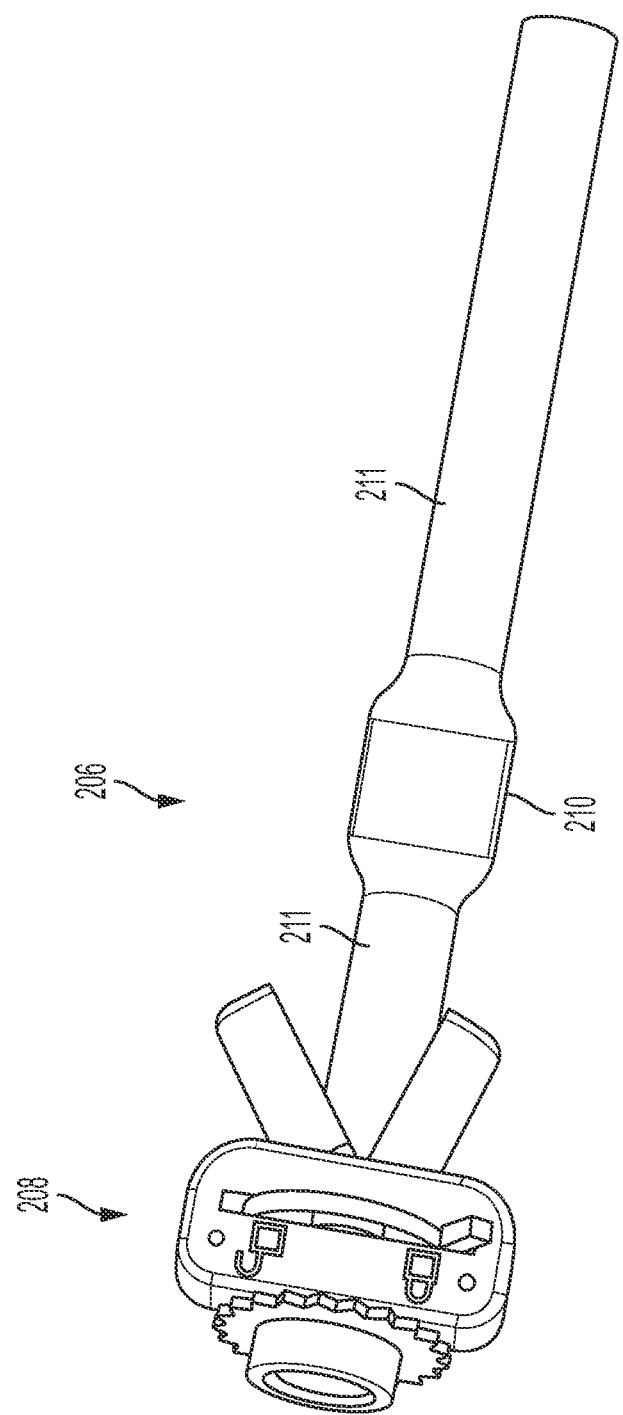
FIG. 19 is a side perspective view schematic representation of an obturator of the portal saver assembly of FIG. 18.

Turning now to FIGS. 18-22, there are shown various views of a portal saver assembly 200, according to another alternative embodiment. As shown in FIG. 18, the portal saver assembly 200 includes a proximal handpiece 202 configured to removably attach to a distal obturator 204. The obturator 204 can be removably connected to a distal tube-like (cannulated) flexible body 206 extending from a proximal seal assembly 208. The flexible body 206 can be composed of TPU and can have the same features and be used in the same fashion as the flexible body 11 described above with reference to FIGS. 2A-2D. The flexible body 206 has a flattened (or narrow) section 210 which acts as a seal and be constructed through heat forming processes. The flattened section 210 is heat sealed to make the obturator tube flat. As shown in FIG. 19, the flexible body 206 has two round sections 211 with the flattened section 210 therebetween. The flattened section 210 can be used as an alternative to a welded flat sheet material with seams (as described with the portal saver assembly 10 in FIGS. 1-11). In some situations, the flattened section 210 for the flexible body 206 is preferable to welded seams because the compression force on the flexible body 206 with welded seams creates high frictions, which tends to grab onto instruments within the flexible body 206. This can lead to accidental withdraw of instruments from a portal and can add a dimension (i.e., "noise) to the sense of feel for the surgeon. The flattened section 210 forms a seal between itself and an instrument extending through the flexible body 206. Thus, the flexible body 206 is tighter around the instrument. After the instrument is removed, the flattened section 210 (i.e., the heat pressed or sealed portion) returns to the flat shape. The flattened section 210 also prevents fluid from leaking out of the flexible body 206 from the incision site.

Figure 20:
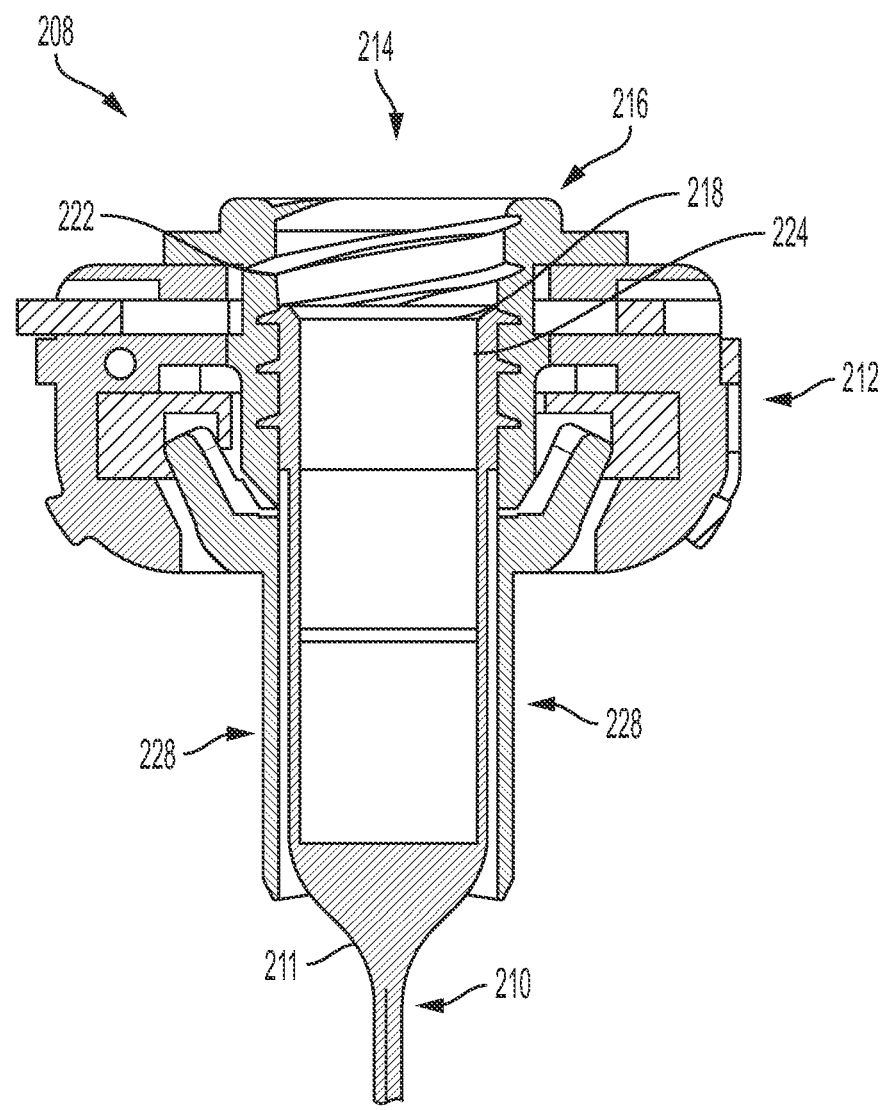
FIG. 20 is a detailed side section view schematic representation of a seal assembly of the obturator of FIG. 19.

Referring now to FIG. 20, there is shown a detailed section view schematic representation of the seal assembly 208, according to an embodiment. The seal assembly 208 comprises a body 212 (e.g., rectangular body) with a central aperture 214 extending through a rotating portion 216 and a non-rotating portion 218. The rotating portion 216 and the non-rotating portion 218 are configured to work in conjunction to fine tune the attachment of the obturator 204 to a tubular body 220 extending through the handpiece 202. The rotating portion 216 is a movable female connector, such as a threaded channel 222 extending from the central aperture 214 as shown. The non-rotating portion 218 is a non-threaded (or relatively smooth) channel 224 connected within the threaded channel 222. The non-threaded channel 222 is also connected to the flexible body 206 near the flattened section 210, as shown in FIG. 18. When the seal assembly 208 is attached to the handpiece 202, the rotating portion 216 and the non-rotating portion 218 receive the tubular body 220 extending through the handpiece 202 (FIG. 18) and the rotating portion 216 is rotated such that the threaded channel 222 tightens around the tubular body 220. In use, instruments can be inserted into a proximal end 226 of the tubular body 220 and pass through the flexible body 206 of the seal assembly 208.

Figure 21:
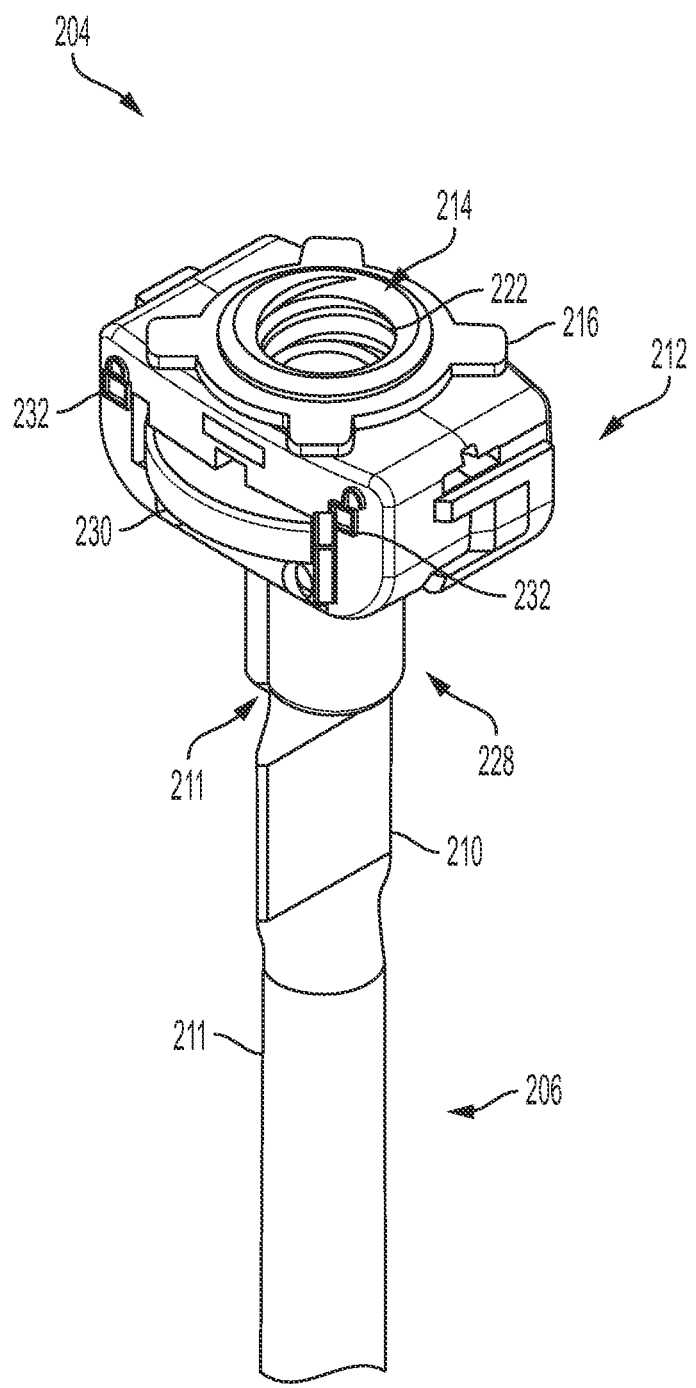
FIG. 21 is a top perspective view schematic representation of the obturator of FIG. 19 in a first configuration.
Figure 22:
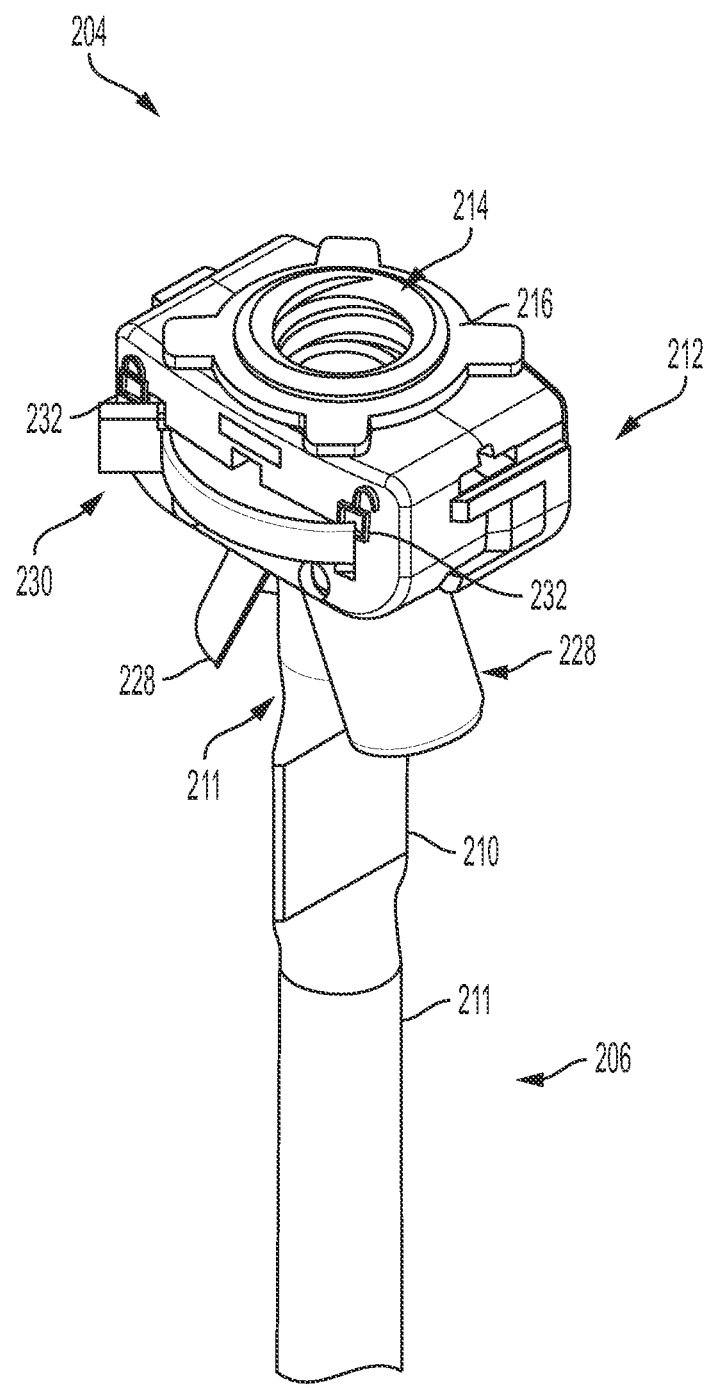
FIG. 22 is a top perspective view schematic representation of the obturator of FIG. 19 in a second configuration.

As shown in FIGS. 21-22, one or more petals 228 extend distally from within the body 212 of the seal assembly 208. The petals 228 are movable from a first configuration to a second configuration using an actuator 230 on the body 212. Referring briefly to FIG. 21, the petals 228 are in the first configuration, closed against the flexible body 206. In the depicted embodiment, the petals 228 extend in a direction parallel to a length of the flexible body 206 in the first configuration. When the petals 228 are in the first configuration, the actuator 230 is in a first position, as shown. In an embodiment, the first position is the unlocked position wherein the petals 228 are approximately flush with the flexible body 206 for insertion into the patient.

Turning now to FIG. 22, the petals 228 are in the second configuration. To move the petals 228 into the second configuration, the actuator 230 is activated. In the depicted embodiment, the actuator 230 is rotated or otherwise moved to a second position. (The first and second positions of the actuator 230 can be denoted by indicators 232 on the 212, as shown). When the petals 228 are in the second configuration, they are expanded and extending at an angle relative to the flexible body 206, as shown. In the second configuration, the petals 228 function to retain the portal saver assembly 200 within the patient.

In use, the obturator 204 is attached to the proximal handpiece 202 using the rotating portion 216 and non-rotating portion 218, as described above. The length of the flexible body 206 can be trimmed (within an 11 mm range, for example) prior to insertion into the incision site. The portal saver assembly 200 is partially advanced into the incision site without posing any risk to surrounding structures (e.g., femoral head) due to its small diameter. (The portal saver assembly 200 can be configured for the dermal openings used in most procedures, including a 12 mm dermal opening diameter, which is smaller than that used for most cannulas). The portal saver assembly 200 (flexible body 206) is advanced farther until the petals 228 are in the dermal layer. The actuator 230 is then moved from the first position to the second position, deploying the petals 228 and moving them from the first configuration to the second configuration. At any time, the length of the flexible body 206 can be trimmed to fine-tune and adjust the length. The proximal handpiece 202 can be removed from the obturator by unscrewing the rotating portion 216. When the surgical procedure is complete, the petals 228 can be moved back to the first configuration (via the actuator 230) and the obturator 202 and flexible body 206 can be passed back through the original incision for easy removal without causing additional trauma or scarring to the skin or dermis of the patient.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. An obturator comprising:
   an obturator body extending along a central longitudinal axis and having a cannulated outer obturator tube extending therethrough, the outer obturator tube having a distal tip with a dilating assembly movable between a collapsed, first configuration and an expanded, second configuration;
   a shaft expander comprising a cannulated inner obturator tube which is movable between a first position and a second position within the outer obturator tube;
   a second cannulated tube having a central longitudinal axis which extends around the cannulated outer obturator tube distal the obturator body;
   a pair of stirrups comprising a first stirrup and a second stirrup, each of which comprises a first portion extending proximally from the second cannulated tube at an angle to the central longitudinal axis and a second portion extending proximally from the respective first portion along an axis parallel to the central longitudinal axis;
   a rigid body connected around the second cannulated tube and moveable along a length of the second cannulated tube;
   wherein in the first position, the inner obturator tube is retracted from the distal tip of the outer obturator tube and the dilating assembly is in the first configuration;
   wherein in the second position, the inner obturator tube is advanced within the distal tip of the outer obturator tube and the dilating assembly is in the second configuration; and
   wherein the rigid body comprises a proximal telescoping assembly, the proximal telescoping assembly comprising one or more blades structured and configured to form an elongated slit in the second cannulated tube parallel to the central longitudinal axis when the rigid body is advanced distally along the length of the second cannulated tube.

2. The obturator of claim 1, wherein the dilating assembly is a duck bill portion at the distal tip of the outer obturator tube, the duck bill portion having at least two arms composed of the outer obturator tube.

3. The obturator of claim 2, further comprising a post on the inner obturator tube which forces the at least two arms radially outward from the collapsed, first configuration to the expanded, second configuration.

4. The obturator of claim 1, wherein the outer obturator tube extends past a distal end of the obturator body.

5. The obturator of claim 4, wherein the second cannulated tube is composed of a flat sheet material with a pair of seams extending along a length of the second cannulated tube.

6. The obturator of claim 4, wherein the second cannulated tube has a flattened section between two rounded sections.

7. The obturator of claim 1, wherein the pair of stirrups is removably attached to the obturator body via one or more connectors.

8. The obturator of claim 7, further comprising a stirrup release actuator on the obturator body configured to release the pair of stirrups from the one or more connectors.

9. The obturator of claim 1, wherein the rigid body comprises distal exterior barbs extending in a direction orthogonal to the central longitudinal axis.

* * * * *